(12) United States Patent
Tanaka et al.

(10) Patent No.: US 8,852,942 B2
(45) Date of Patent: Oct. 7, 2014

(54) CINERARIA-DERIVED CHROMOSOMAL DNA INVOLVED IN SYNTHESIS OF FLAVONOID, AND USE THEREOF

(75) Inventors: Yoshikazu Tanaka, Mishima-gun (JP); Filippa Brugliera, Preston (AU)

(73) Assignee: Suntory Holdings Limited, Osaka-shi, Osaka (JP)

(*) Notice: Subject to any disclaimer, the term of this patent is extended or adjusted under 35 U.S.C. 154(b) by 632 days.

(21) Appl. No.: 13/124,985

(22) PCT Filed: Oct. 26, 2009

(86) PCT No.: PCT/JP2009/068736
§ 371 (c)(1),
(2), (4) Date: Apr. 19, 2011

(87) PCT Pub. No.: WO2010/050605
PCT Pub. Date: May 6, 2010

(65) Prior Publication Data
US 2011/0219477 A1 Sep. 8, 2011

(30) Foreign Application Priority Data
Oct. 27, 2008 (JP) ................. 2008-276029

(51) Int. Cl.
| | | |
|---|---|---|
| C12N 15/00 | (2006.01) | |
| C12N 5/04 | (2006.01) | |
| C12N 5/10 | (2006.01) | |
| C12N 1/20 | (2006.01) | |
| C07H 21/04 | (2006.01) | |
| C12N 9/02 | (2006.01) | |
| C12N 15/82 | (2006.01) | |

(52) U.S. Cl.
CPC ........... *A12N 15/825* (2013.01); *C12N 9/0073* (2013.01); *C12N 15/8225* (2013.01)
USPC ............... 435/419; 435/320.1; 435/252.3; 536/24.1

(58) Field of Classification Search
USPC ........................................... 800/282
See application file for complete search history.

(56) References Cited

U.S. PATENT DOCUMENTS

| | | | | |
|---|---|---|---|---|
| 6,080,920 A | | 6/2000 | Holton | |
| 8,288,612 B2 * | | 10/2012 | Brugliera | ............ 800/282 |

FOREIGN PATENT DOCUMENTS

| | | |
|---|---|---|
| JP | 8-511683 | 12/1996 |
| JP | 11-505116 | 5/1999 |
| JP | 11-178572 | 7/1999 |
| JP | 2003-159078 | 6/2003 |
| WO | 94/28140 | 12/1994 |
| WO | 96/36716 | 11/1996 |
| WO | 2009/062253 | 5/2009 |
| WO | WO 2009/062259 A1 | 5/2009 |

OTHER PUBLICATIONS

Toguri et al. (Agrobacterium-mediated Transformation of *Chrysanthemum* (*Dendranthema grandiflora*) Plants with a Disease Resistance Gene (pac1), 20 Plant Biotechnology, 121-127 (2003)).*
Hill et al. (Discrete spatial and temporal cis-acting elements regulate transcription of the *Arabidopsis* floral homeotic gene APETALA3, 125 Development, 1711-1721 (1998)).*
Machine translation of Yamamura et al., JP 2003159078A, published Jun. 3, 2003; available at http://worldwide.espacenet.com/publicationDetails/biblio?CC=JP&NR=2003159078A&KC=A&FT=D&ND=5&date=20030603&DB=EPODOC&locale=en_EP.*
International Search Report issued on Nov. 24, 2009 in International Application No. PCT/JP2009/068736 filed Oct. 26, 2009.
GenBank Accession No. AY791885 to "*Pericallis cruenta* flavonoid-3', 5'-hydroxylase mRNA, complete cds.", Database DDBJ/EMBL/GenBank [online], [GI: 60550199], <URL: http://www.ncbi.nlm.gov/sviewer/viewer.fcgi?60550199:NCBI: 10040433>, May 1, 2005 uploaded [retrieved on Nov. 11, 2009].
Hitoshi Kobayashi et al., "Flower-specific gene expression directed by the promoter of a chalcone systhase gene from *Gentiana triflora* in *Petunia hybrida*," Plant Science, 1998, vol. 131, No. 2, pp. 173-180, Elsevier Science Ireland Ltd.
Christian Seitz et al., "Cloning, functional identification and sequence analysis of flavonoid 3'-hydroxylase and flavonoid 3',5'-hydroxylase cDNAs reveals independent evolution of flavonoid 3',5'-hydroxylase in the Asteraceae family," Plant Molecular Biology, 2006, vol. 61, No. 3, pp. 365-381, Springer.
Yoshikazu Tanaka, "Flower colour and cytochromes P450", Phytochem. Rev., 2006, 5: pp. 283-291.
Yukihisa Katsumoto et al., "Engineering of the Rose Flavonoid Biosynthetic Pathway Successfully Generated Blue-Hued Flowers Accumulating Delphinidin", Plant Cell Physiol., 48(11), 2007, pp. 1589-1600.
Yoshikazu Tanaka et al., "Seeing is believing: engineering anthocyanin and carotenoid biosynthetic pathways", Current Opinion in Biotechnology, 2008, 19, pp. 190-197.
Shinzo Tsuda et al., "Flower color modification of *Petunia hybrida* commercial varieties by metabolic engineering", Plant Biotechnology, 21(5), 2004, pp. 377-386.
Smith et al., "Total silencing by intron-spliced hairpin RNAs", Nature, vol. 407, Sep. 21, 2000, pp. 319-320.
Yoshikazu Tanaka et al., "Genetic engineering in floriculture", Plant Cell, Tissue and Organ Culture, vol. 80, No. 1, Jan. 1, 2005, pp. 1-24.
Supplementary European Search Report mailed Apr. 4, 2012 issued in European Application No. 09823715.9 filed Oct. 26, 2009.

* cited by examiner

Primary Examiner — Ashwin Mehta
Assistant Examiner — Rebecca Coobs
(74) *Attorney, Agent, or Firm* — Drinker Biddle & Reath LLP

(57) ABSTRACT

Presently provided are a *cineraria*-derived polynucleotide which can act as a promoter for a coding region of flavonoid 3',5'-hydroxylase (F3'5'H and a F3'5'H gene construct which carries the polynucleotide. The *cineraria*-derived petal-specific promoter can be as polynucleotide having the nucleotide sequence depicted in SEQ ID NO: 9 or a polynucleotide which can hybridize with the polynucleotide having the nucleotide sequence depicted in SEQ ID NO: 9 under stringent conditions and can act as a promoter for a coding region of flavonoid. 3',5'-hydroxylase (F3'5'H). The gene construct can be used, for inhibiting the expression of a gene in an RNAi method, which has, as a loop, a polynucleotide comprising the whole or a part of a first intron of the presently provided *cineraria*-derived polynucleotide.

4 Claims, 5 Drawing Sheets

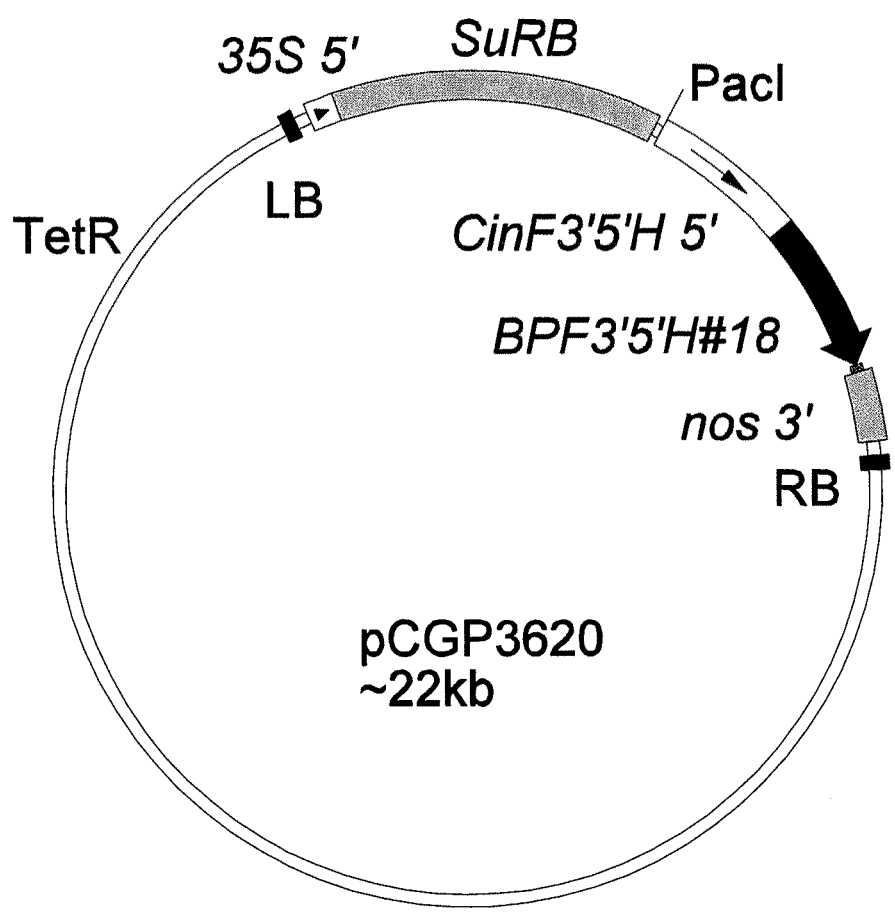

```
                        SEQUENCE LISTING

<160> NUMBER OF SEQ ID NOS: 14

<210> SEQ ID NO 1
<211> LENGTH: 1674
<212> TYPE: DNA
<213> ORGANISM: Senecio cruentus
<220> FEATURE:
<221> NAME/KEY: misc_feature
<223> OTHER INFORMATION: Ci5a13
<220> FEATURE:
<221> NAME/KEY: CDS
<222> LOCATION: (12)..(1541)

<400> SEQUENCE: 1
gcttatttga a atg act att cta acc ctt gtt ctc tac act tgc ctc act      50
            Met Thr Ile Leu Thr Leu Val Leu Tyr Thr Cys Leu Thr
              1               5                  10 ggg gta gca ttc tac gcg ttg ctt aaa ctg ttt aca cgt cat cct aac       98
Gly Val Ala Phe Tyr Ala Leu Leu Lys Leu Phe Thr Arg His Pro Asn
 15                  20                  25 cgt ctt ccc cct ggt cca acc cca tgg ccg gtt gtt gga aac ctg cca      146
Arg Leu Pro Pro Gly Pro Thr Pro Trp Pro Val Val Gly Asn Leu Pro
 30                  35                  40                  45 cac ctt ggt tct att ccg cat cac ggg ctg gct gcc ttg gca acc aag      194
His Leu Gly Ser Ile Pro His His Gly Leu Ala Ala Leu Ala Thr Lys
                 50                  55                  60 tat ggc ccg ttg atg cac ctt agg ctc ggg ttt gtt gac gtg gtg gtt      242
Tyr Gly Pro Leu Met His Leu Arg Leu Gly Phe Val Asp Val Val Val
             65                  70                  75 gcc gcg tct gcg tcc gta gct gca cag ttt tta aag gtt cat gac gcg      290
Ala Ala Ser Ala Ser Val Ala Ala Gln Phe Leu Lys Val His Asp Ala
         80                  85                  90 aat ttc gct agt aga ccg ccg aat tct gga gcc aag cat atg gcg tat      338
Asn Phe Ala Ser Arg Pro Pro Asn Ser Gly Ala Lys His Met Ala Tyr
     95                 100                 105 aat tat cag gat ttg gtg ttt gca ccg tat ggt cca agg tgg cga atg      386
Asn Tyr Gln Asp Leu Val Phe Ala Pro Tyr Gly Pro Arg Trp Arg Met
110                 115                 120                 125 ctt agg aag att tgc tcg gtg cac ttg ttt tcg gcg aaa gct ctt gat      434
Leu Arg Lys Ile Cys Ser Val His Leu Phe Ser Ala Lys Ala Leu Asp
                130                 135                 140 gat ttt cgt cat gtt cga cag gag gag gta gcg acc ctc acg cgc aat      482
Asp Phe Arg His Val Arg Gln Glu Glu Val Ala Thr Leu Thr Arg Asn
            145                 150                 155 tta ctt ggt gcc gaa aga tca ccg gtg aaa tta ggc caa cta ctt aac      530
Leu Leu Gly Ala Glu Arg Ser Pro Val Lys Leu Gly Gln Leu Leu Asn
        160                 165                 170 gtg tgc acc aca aac gcg tta gcg cga gtg atg tta ggc aag aga gta      578
Val Cys Thr Thr Asn Ala Leu Ala Arg Val Met Leu Gly Lys Arg Val
    175                 180                 185 ttc gga agt ggt ggt ggt gat ccg aag gca gat gaa ttt aag gat atg      626
Phe Gly Ser Gly Gly Gly Asp Pro Lys Ala Asp Glu Phe Lys Asp Met
190                 195                 200                 205 gtt gtt gaa atg atg gtt ctg gcc gga gaa ttc aat cta ggt gat ttc      674
Val Val Glu Met Met Val Leu Ala Gly Glu Phe Asn Leu Gly Asp Phe
                210                 215                 220 att ccc gtg ctt gat tgg ctt gac ttg caa ggt atc acg aaa aag atg      722
Ile Pro Val Leu Asp Trp Leu Asp Leu Gln Gly Ile Thr Lys Lys Met
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 225 |     |     |     |     | 230 |     |     |     |     | 235 |     |      |
| aaa | aaa | gtc | cat | agg | cga | ttt | gat | tcg | ttc | ctt | agc | aag | att | ctt | gac | 770  |
| Lys | Lys | Val | His | Arg | Arg | Phe | Asp | Ser | Phe | Leu | Ser | Lys | Ile | Leu | Asp |      |
|     |     | 240 |     |     |     |     | 245 |     |     |     |     | 250 |     |     |     |      |
| gaa | cat | aag | gtc | ggc | gag | gat | ggt | gcg | tcg | ggt | cat | aga | gac | ttg | ttg | 818  |
| Glu | His | Lys | Val | Gly | Glu | Asp | Gly | Ala | Ser | Gly | His | Arg | Asp | Leu | Leu |      |
|     | 255 |     |     |     |     | 260 |     |     |     |     | 265 |     |     |     |     |      |
| agc | act | ttg | att | tcg | gtc | aag | gat | gac | gcg | gat | gga | gag | gga | ggg | aag | 866  |
| Ser | Thr | Leu | Ile | Ser | Val | Lys | Asp | Asp | Ala | Asp | Gly | Glu | Gly | Gly | Lys |      |
| 270 |     |     |     |     | 275 |     |     |     |     | 280 |     |     |     |     | 285 |      |
| ctt | tcc | gat | agc | gaa | atc | aaa | gct | ttg | ctt | ttg | aat | tta | ttc | gtt | gcg | 914  |
| Leu | Ser | Asp | Ser | Glu | Ile | Lys | Ala | Leu | Leu | Leu | Asn | Leu | Phe | Val | Ala |      |
|     |     |     |     | 290 |     |     |     |     | 295 |     |     |     |     | 300 |     |      |
| gga | aca | gac | acg | tca | tct | agt | acc | gta | gaa | tgg | gcg | ata | gcc | gag | ctg | 962  |
| Gly | Thr | Asp | Thr | Ser | Ser | Ser | Thr | Val | Glu | Trp | Ala | Ile | Ala | Glu | Leu |      |
|     |     |     | 305 |     |     |     |     | 310 |     |     |     |     | 315 |     |     |      |
| att | cgc | aac | cca | cgc | cta | atg | aaa | caa | gcc | caa | gaa | gaa | ata | gac | aac | 1010 |
| Ile | Arg | Asn | Pro | Arg | Leu | Met | Lys | Gln | Ala | Gln | Glu | Glu | Ile | Asp | Asn |      |
|     |     | 320 |     |     |     |     | 325 |     |     |     |     | 330 |     |     |     |      |
| gta | gtt | ggt | cgt | gac | cgg | gtt | gta | acc | gaa | ttg | gat | cta | agc | caa | cta | 1058 |
| Val | Val | Gly | Arg | Asp | Arg | Val | Val | Thr | Glu | Leu | Asp | Leu | Ser | Gln | Leu |      |
|     | 335 |     |     |     |     | 340 |     |     |     |     | 345 |     |     |     |     |      |
| aca | ttc | ctc | cag | gct | gtt | gtg | aag | gag | acc | ttt | agg | ctc | cac | cca | tcg | 1106 |
| Thr | Phe | Leu | Gln | Ala | Val | Val | Lys | Glu | Thr | Phe | Arg | Leu | His | Pro | Ser |      |
| 350 |     |     |     |     | 355 |     |     |     |     | 360 |     |     |     |     | 365 |      |
| aca | cca | ctc | tct | tta | cca | agg | att | gca | tcg | gag | agt | tgt | gag | atc | aac | 1154 |
| Thr | Pro | Leu | Ser | Leu | Pro | Arg | Ile | Ala | Ser | Glu | Ser | Cys | Glu | Ile | Asn |      |
|     |     |     |     | 370 |     |     |     |     | 375 |     |     |     |     | 380 |     |      |
| aga | tat | cat | att | cct | aag | gga | tcc | acg | ctc | ctt | gtt | aac | gtg | tgg | gcc | 1202 |
| Arg | Tyr | His | Ile | Pro | Lys | Gly | Ser | Thr | Leu | Leu | Val | Asn | Val | Trp | Ala |      |
|     |     |     | 385 |     |     |     |     | 390 |     |     |     |     | 395 |     |     |      |
| att | gcc | cga | gac | cca | aaa | atg | tgg | acc | gac | cca | ctt | gag | ttc | aag | ccc | 1250 |
| Ile | Ala | Arg | Asp | Pro | Lys | Met | Trp | Thr | Asp | Pro | Leu | Glu | Phe | Lys | Pro |      |
|     |     | 400 |     |     |     |     | 405 |     |     |     |     | 410 |     |     |     |      |
| gct | cgt | ttc | tta | cct | ggt | ggt | gaa | aag | gcc | gat | gta | gat | gtt | aag | gga | 1298 |
| Ala | Arg | Phe | Leu | Pro | Gly | Gly | Glu | Lys | Ala | Asp | Val | Asp | Val | Lys | Gly |      |
|     | 415 |     |     |     |     | 420 |     |     |     |     | 425 |     |     |     |     |      |
| aat | gat | ttc | gaa | gtc | ata | cca | ttt | ggg | gcg | ggc | cgg | agg | att | tgt | gcg | 1346 |
| Asn | Asp | Phe | Glu | Val | Ile | Pro | Phe | Gly | Ala | Gly | Arg | Arg | Ile | Cys | Ala |      |
| 430 |     |     |     |     | 435 |     |     |     |     | 440 |     |     |     |     | 445 |      |
| ggt | ata | agt | cta | ggg | atg | aga | atg | gtc | caa | tta | ctt | att | gca | aca | ttg | 1394 |
| Gly | Ile | Ser | Leu | Gly | Met | Arg | Met | Val | Gln | Leu | Leu | Ile | Ala | Thr | Leu |      |
|     |     |     |     | 450 |     |     |     |     | 455 |     |     |     |     | 460 |     |      |
| gtc | caa | acc | ttt | gat | tgg | gaa | ttg | gct | aat | ggt | tta | ttg | cca | gag | aag | 1442 |
| Val | Gln | Thr | Phe | Asp | Trp | Glu | Leu | Ala | Asn | Gly | Leu | Leu | Pro | Glu | Lys |      |
|     |     |     | 465 |     |     |     |     | 470 |     |     |     |     | 475 |     |     |      |
| ctc | aac | atg | gat | gaa | gcc | tat | ggg | cta | acc | ctt | caa | agg | gct | tca | cct | 1490 |
| Leu | Asn | Met | Asp | Glu | Ala | Tyr | Gly | Leu | Thr | Leu | Gln | Arg | Ala | Ser | Pro |      |
|     |     | 480 |     |     |     |     | 485 |     |     |     |     | 490 |     |     |     |      |
| ttg | atg | gtg | cac | cca | agg | ccc | agg | tta | gcc | cca | cac | gta | tac | gga | agt | 1538 |
| Leu | Met | Val | His | Pro | Arg | Pro | Arg | Leu | Ala | Pro | His | Val | Tyr | Gly | Ser |      |
|     | 495 |     |     |     |     | 500 |     |     |     |     | 505 |     |     |     |     |      | ggt tagggagtac attgtaggtt tttttactaa taaaataaaa tgttatattt    1591
Gly
510 tacaaatggt tatttatct tttgtattta ctactgtctg aattgtttgt attttgattt    1651 ggttaaaaaa aaaaaaaaaa aaa    1674

<210> SEQ ID NO 2
<211> LENGTH: 510
<212> TYPE: PRT
<213> ORGANISM: Senecio cruentus

<400> SEQUENCE: 2

| Met | Thr | Ile | Leu | Thr | Leu | Val | Leu | Tyr | Thr | Cys | Leu | Thr | Gly | Val | Ala |
|---|---|---|---|---|---|---|---|---|---|---|---|---|---|---|---|
| 1 | | | | 5 | | | | | 10 | | | | | 15 | |

| Phe | Tyr | Ala | Leu | Leu | Lys | Leu | Phe | Thr | Arg | His | Pro | Asn | Arg | Leu | Pro |
| | | | 20 | | | | | 25 | | | | | 30 | | |

| Pro | Gly | Pro | Thr | Pro | Trp | Pro | Val | Val | Gly | Asn | Leu | Pro | His | Leu | Gly |
| | | | 35 | | | | | 40 | | | | | 45 | | |

| Ser | Ile | Pro | His | His | Gly | Leu | Ala | Ala | Leu | Ala | Thr | Lys | Tyr | Gly | Pro |
| | | 50 | | | | | 55 | | | | | 60 | | | |

| Leu | Met | His | Leu | Arg | Leu | Gly | Phe | Val | Asp | Val | Val | Ala | Ala | Ser |
| 65 | | | | | 70 | | | | | 75 | | | | | 80 |

| Ala | Ser | Val | Ala | Ala | Gln | Phe | Leu | Lys | Val | His | Asp | Ala | Asn | Phe | Ala |
| | | | | 85 | | | | | 90 | | | | | 95 | |

| Ser | Arg | Pro | Pro | Asn | Ser | Gly | Ala | Lys | His | Met | Ala | Tyr | Asn | Tyr | Gln |
| | | | 100 | | | | | 105 | | | | | 110 | | |

| Asp | Leu | Val | Phe | Ala | Pro | Tyr | Gly | Pro | Arg | Trp | Arg | Met | Leu | Arg | Lys |
| | | | 115 | | | | | 120 | | | | | 125 | | |

| Ile | Cys | Ser | Val | His | Leu | Phe | Ser | Ala | Lys | Ala | Leu | Asp | Asp | Phe | Arg |
| | | 130 | | | | | 135 | | | | | 140 | | | |

| His | Val | Arg | Gln | Glu | Glu | Val | Ala | Thr | Leu | Thr | Arg | Asn | Leu | Leu | Gly |
| 145 | | | | | 150 | | | | | 155 | | | | | 160 |

| Ala | Glu | Arg | Ser | Pro | Val | Lys | Leu | Gly | Gln | Leu | Leu | Asn | Val | Cys | Thr |
| | | | | 165 | | | | | 170 | | | | | 175 | |

| Thr | Asn | Ala | Leu | Ala | Arg | Val | Met | Leu | Gly | Lys | Arg | Val | Phe | Gly | Ser |
| | | | 180 | | | | | 185 | | | | | 190 | | |

| Gly | Gly | Gly | Asp | Pro | Lys | Ala | Asp | Glu | Phe | Lys | Asp | Met | Val | Val | Glu |
| | | 195 | | | | | 200 | | | | | 205 | | | |

| Met | Met | Val | Leu | Ala | Gly | Glu | Phe | Asn | Leu | Gly | Asp | Phe | Ile | Pro | Val |
| 210 | | | | | 215 | | | | | 220 | | | | | |

| Leu | Asp | Trp | Leu | Asp | Leu | Gln | Gly | Ile | Thr | Lys | Lys | Met | Lys | Lys | Val |
| 225 | | | | | 230 | | | | | 235 | | | | | 240 |

| His | Arg | Arg | Phe | Asp | Ser | Phe | Leu | Ser | Lys | Ile | Leu | Asp | Glu | His | Lys |
| | | | | 245 | | | | | 250 | | | | | 255 | |

| Val | Gly | Glu | Asp | Gly | Ala | Ser | Gly | His | Arg | Asp | Leu | Leu | Ser | Thr | Leu |
| | | | 260 | | | | | 265 | | | | | 270 | | |

| Ile | Ser | Val | Lys | Asp | Asp | Ala | Asp | Gly | Glu | Gly | Gly | Lys | Leu | Ser | Asp |
| | | | 275 | | | | | 280 | | | | | 285 | | |

| Ser | Glu | Ile | Lys | Ala | Leu | Leu | Leu | Asn | Leu | Phe | Val | Ala | Gly | Thr | Asp |
| | | | 290 | | | | | 295 | | | | | 300 | | |

| Thr | Ser | Ser | Ser | Thr | Val | Glu | Trp | Ala | Ile | Ala | Glu | Leu | Ile | Arg | Asn |
| 305 | | | | | 310 | | | | | 315 | | | | | 320 |

| Pro | Arg | Leu | Met | Lys | Gln | Ala | Gln | Glu | Glu | Ile | Asp | Asn | Val | Val | Gly |
| | | | | 325 | | | | | 330 | | | | | 335 | |

| Arg | Asp | Arg | Val | Val | Thr | Glu | Leu | Asp | Leu | Ser | Gln | Leu | Thr | Phe | Leu |
| | | | 340 | | | | | 345 | | | | | 350 | | |

| Gln | Ala | Val | Val | Lys | Glu | Thr | Phe | Arg | Leu | His | Pro | Ser | Thr | Pro | Leu |
| | | | | 355 | | | | | 360 | | | | | 365 | |

| Ser | Leu | Pro | Arg | Ile | Ala | Ser | Glu | Ser | Cys | Glu | Ile | Asn | Arg | Tyr | His |
| | | 370 | | | | | 375 | | | | | 380 | | | |

```
Ile Pro Lys Gly Ser Thr Leu Leu Val Asn Val Trp Ala Ile Ala Arg
385                 390                 395                 400

Asp Pro Lys Met Trp Thr Asp Pro Leu Glu Phe Lys Pro Ala Arg Phe
            405                 410                 415

Leu Pro Gly Gly Glu Lys Ala Asp Val Asp Val Lys Gly Asn Asp Phe
            420                 425                 430

Glu Val Ile Pro Phe Gly Ala Gly Arg Arg Ile Cys Ala Gly Ile Ser
            435                 440                 445

Leu Gly Met Arg Met Val Gln Leu Leu Ile Ala Thr Leu Val Gln Thr
    450                 455                 460

Phe Asp Trp Glu Leu Ala Asn Gly Leu Leu Pro Glu Lys Leu Asn Met
465                 470                 475                 480

Asp Glu Ala Tyr Gly Leu Thr Leu Gln Arg Ala Ser Pro Leu Met Val
                485                 490                 495

His Pro Arg Pro Arg Leu Ala Pro His Val Tyr Gly Ser Gly
            500                 505                 510

<210> SEQ ID NO 3
<211> LENGTH: 1667
<212> TYPE: DNA
<213> ORGANISM: Senecio cruentus
<220> FEATURE:
<221> NAME/KEY: misc_feature
<223> OTHER INFORMATION: Ci5a18
<220> FEATURE:
<221> NAME/KEY: CDS
<222> LOCATION: (39)..(1550)

<400> SEQUENCE: 3
gaattactaa ccaattctta cgttgtcaag taaataaa atg agc att cta acc cta       56
                                          Met Ser Ile Leu Thr Leu
                                          1               5 atc tgc acc ttc atc act ggt ttg atg ttc tat ggg ttg gtt aat ttg      104
Ile Cys Thr Phe Ile Thr Gly Leu Met Phe Tyr Gly Leu Val Asn Leu
            10                  15                  20 ctt agc cgt cgc gct agc cgt ctt cct cca ggt cca acc cca tgg cca      152
Leu Ser Arg Arg Ala Ser Arg Leu Pro Pro Gly Pro Thr Pro Trp Pro
        25                  30                  35 atc atc ggc aac cta atg cac ctt ggt aaa ctt cca cat cac tcg ctg      200
Ile Ile Gly Asn Leu Met His Leu Gly Lys Leu Pro His His Ser Leu
    40                  45                  50 gcg gac ttg gcg aaa aag tat ggt ccg ttg ata cat gtc cga cta ggg      248
Ala Asp Leu Ala Lys Lys Tyr Gly Pro Leu Ile His Val Arg Leu Gly
55                  60                  65                  70 tcc gtt gat gtt gtg gtg gcc tcg tct gcg tcc gtt gct ggg cag ttt      296
Ser Val Asp Val Val Ala Ser Ser Ala Ser Val Ala Gly Gln Phe
                75                  80                  85 tta aag gtg cac gat gcg aat ttt gcc aac agg cca cca aat tct gga      344
Leu Lys Val His Asp Ala Asn Phe Ala Asn Arg Pro Pro Asn Ser Gly
            90                  95                  100 gct aaa cat atg gcg tat aat tat cat gat atg gtg ttt gcg ccg tat      392
Ala Lys His Met Ala Tyr Asn Tyr His Asp Met Val Phe Ala Pro Tyr
        105                 110                 115 ggt cca agg tgg cga atg ctt cga aag atg tgc tcc atg cat ctg ttt      440
Gly Pro Arg Trp Arg Met Leu Arg Lys Met Cys Ser Met His Leu Phe
    120                 125                 130 tct gcc aaa gca ctc act gat ttt cgt caa gtt cga cag gag gag gta      488
Ser Ala Lys Ala Leu Thr Asp Phe Arg Gln Val Arg Gln Glu Glu Val
135                 140                 145                 150 atg ata ctc acg cgc gtt ttg gcc ggg act gaa caa tcg gca gtg aaa      536
Met Ile Leu Thr Arg Val Leu Ala Gly Thr Glu Gln Ser Ala Val Lys
```

```
Met Ile Leu Thr Arg Val Leu Ala Gly Thr Glu Gln Ser Ala Val Lys
            155                 160                 165 cta gat caa caa ctt aac gtg tgc ttc gca aac aca tta tcc cga atg      584
Leu Asp Gln Gln Leu Asn Val Cys Phe Ala Asn Thr Leu Ser Arg Met
        170                 175                 180 atg tta gac agg aga gta ttt gga gac ggt gat cca aag gcg gac gac      632
Met Leu Asp Arg Arg Val Phe Gly Asp Gly Asp Pro Lys Ala Asp Asp
            185                 190                 195 tac aag gat atg gtg gtt gag ttg atg act ttg gcc gga caa ttc aac      680
Tyr Lys Asp Met Val Val Glu Leu Met Thr Leu Ala Gly Gln Phe Asn
    200                 205                 210 atc ggt gac tac att cct tgg ctt gac ttg ctt gac cta caa ggc att      728
Ile Gly Asp Tyr Ile Pro Trp Leu Asp Leu Leu Asp Leu Gln Gly Ile
215                 220                 225                 230 gtc aaa agg atg aag aaa gtt cat tct caa ttc gat tcg ttc ctt gac      776
Val Lys Arg Met Lys Lys Val His Ser Gln Phe Asp Ser Phe Leu Asp
            235                 240                 245 acc atc att gat gaa cat act att ggc acg ggc cgt cat gtt gac atg      824
Thr Ile Ile Asp Glu His Thr Ile Gly Thr Gly Arg His Val Asp Met
        250                 255                 260 tta agc aca atg att tca ctc aaa gat aat gcc gat gga gag gga ggg      872
Leu Ser Thr Met Ile Ser Leu Lys Asp Asn Ala Asp Gly Glu Gly Gly
            265                 270                 275 aag ctt tcg ttc atc gag atc aaa gct ctt cta ctg aac tta ttc tca      920
Lys Leu Ser Phe Ile Glu Ile Lys Ala Leu Leu Leu Asn Leu Phe Ser
    280                 285                 290 gcg gga acg gac acg tca tct agt acc gtg gaa tgg gga ata gcg gaa      968
Ala Gly Thr Asp Thr Ser Ser Ser Thr Val Glu Trp Gly Ile Ala Glu
295                 300                 305                 310 ctc att cgc cac cca cag cta atg aaa caa gcg caa gaa gaa atg gac     1016
Leu Ile Arg His Pro Gln Leu Met Lys Gln Ala Gln Glu Glu Met Asp
            315                 320                 325 att gta att gga aaa aac cgg ctt gta aca gaa atg gac ata agc caa     1064
Ile Val Ile Gly Lys Asn Arg Leu Val Thr Glu Met Asp Ile Ser Gln
        330                 335                 340 cta aca ttc ctc caa gcc att gtg aaa gaa acg ttt aga ctc cac ccc     1112
Leu Thr Phe Leu Gln Ala Ile Val Lys Glu Thr Phe Arg Leu His Pro
            345                 350                 355 gcg acg cca ctt tcc ctg cca agg att gca tcg gaa agc tgt gag gtc     1160
Ala Thr Pro Leu Ser Leu Pro Arg Ile Ala Ser Glu Ser Cys Glu Val
    360                 365                 370 aag ggg tat cat gtt cct aag gga tcc ata ctc ttt gtt aac gtg tgg     1208
Lys Gly Tyr His Val Pro Lys Gly Ser Ile Leu Phe Val Asn Val Trp
375                 380                 385                 390 gcc att gct cga caa tca gaa ttg tgg acc gac cca ctt gaa ttt cgg     1256
Ala Ile Ala Arg Gln Ser Glu Leu Trp Thr Asp Pro Leu Glu Phe Arg
            395                 400                 405 cct ggt cgt ttc cta atc cca gga gaa aaa cct aat gtt gaa gtg aag     1304
Pro Gly Arg Phe Leu Ile Pro Gly Glu Lys Pro Asn Val Glu Val Lys
        410                 415                 420 cca aat gat ttc gaa att gta cca ttc ggg gga gga cga agg att tgt     1352
Pro Asn Asp Phe Glu Ile Val Pro Phe Gly Gly Gly Arg Arg Ile Cys
            425                 430                 435 gca ggt atg agc ctc gga ttg aga atg gtc aat ttg ctt att gca aca     1400
Ala Gly Met Ser Leu Gly Leu Arg Met Val Asn Leu Leu Ile Ala Thr
    440                 445                 450 ttg gtt caa gcc ttt gat tgg gaa ttg gct aat ggg tta gag cca gaa     1448
Leu Val Gln Ala Phe Asp Trp Glu Leu Ala Asn Gly Leu Glu Pro Glu
455                 460                 465                 470
```

```
aag ctt aac atg gaa gaa gtg ttt ggg att agc ctt caa agg gtt caa      1496
Lys Leu Asn Met Glu Glu Val Phe Gly Ile Ser Leu Gln Arg Val Gln
             475                 480                 485 ccc ttg ttg gtg cac ccg agg cca agg tta gcc cgt cac gta tac gga      1544
Pro Leu Leu Val His Pro Arg Pro Arg Leu Ala Arg His Val Tyr Gly
             490                 495                 500 acg ggt taaggaaata aactgcctgt ttgtaagata aatctgtttg aatttatgta       1600
Thr Gly ttaaatagtt atgctaagaa ctattttac aaataaagt atattggttt gaaaaaaaa       1660 aaaaaaa                                                               1667

<210> SEQ ID NO 4
<211> LENGTH: 504
<212> TYPE: PRT
<213> ORGANISM: Senecio cruentus

<400> SEQUENCE: 4

Met Ser Ile Leu Thr Leu Ile Cys Thr Phe Ile Thr Gly Leu Met Phe
1               5                   10                  15

Tyr Gly Leu Val Asn Leu Leu Ser Arg Arg Ala Ser Arg Leu Pro Pro
            20                  25                  30

Gly Pro Thr Pro Trp Pro Ile Ile Gly Asn Leu Met His Leu Gly Lys
        35                  40                  45

Leu Pro His His Ser Leu Ala Asp Leu Ala Lys Lys Tyr Gly Pro Leu
    50                  55                  60

Ile His Val Arg Leu Gly Ser Val Asp Val Val Ala Ser Ser Ala
65                  70                  75                  80

Ser Val Ala Gly Gln Phe Leu Lys Val His Asp Ala Asn Phe Ala Asn
                85                  90                  95

Arg Pro Pro Asn Ser Gly Ala Lys His Met Ala Tyr Asn Tyr His Asp
            100                 105                 110

Met Val Phe Ala Pro Tyr Gly Pro Arg Trp Arg Met Leu Arg Lys Met
        115                 120                 125

Cys Ser Met His Leu Phe Ser Ala Lys Ala Leu Thr Asp Phe Arg Gln
    130                 135                 140

Val Arg Gln Glu Glu Val Met Ile Leu Thr Arg Val Leu Ala Gly Thr
145                 150                 155                 160

Glu Gln Ser Ala Val Lys Leu Asp Gln Gln Leu Asn Val Cys Phe Ala
                165                 170                 175

Asn Thr Leu Ser Arg Met Met Leu Asp Arg Arg Val Phe Gly Asp Gly
            180                 185                 190

Asp Pro Lys Ala Asp Asp Tyr Lys Asp Met Val Val Glu Leu Met Thr
        195                 200                 205

Leu Ala Gly Gln Phe Asn Ile Gly Asp Tyr Ile Pro Trp Leu Asp Leu
    210                 215                 220

Leu Asp Leu Gln Gly Ile Val Lys Arg Met Lys Lys Val His Ser Gln
225                 230                 235                 240

Phe Asp Ser Phe Leu Asp Thr Ile Ile Asp Glu His Thr Ile Gly Thr
                245                 250                 255

Gly Arg His Val Asp Met Leu Ser Thr Met Ile Ser Leu Lys Asp Asn
            260                 265                 270

Ala Asp Gly Glu Gly Gly Lys Leu Ser Phe Ile Glu Ile Lys Ala Leu
        275                 280                 285

Leu Leu Asn Leu Phe Ser Ala Gly Thr Asp Thr Ser Ser Ser Thr Val
    290                 295                 300
```

```
Glu Trp Gly Ile Ala Glu Leu Ile Arg His Pro Gln Leu Met Lys Gln
305                 310                 315                 320

Ala Gln Glu Glu Met Asp Ile Val Ile Gly Lys Asn Arg Leu Val Thr
                325                 330                 335

Glu Met Asp Ile Ser Gln Leu Thr Phe Leu Gln Ala Ile Val Lys Glu
            340                 345                 350

Thr Phe Arg Leu His Pro Ala Thr Pro Leu Ser Leu Pro Arg Ile Ala
        355                 360                 365

Ser Glu Ser Cys Glu Val Lys Gly Tyr His Val Pro Lys Gly Ser Ile
    370                 375                 380

Leu Phe Val Asn Val Trp Ala Ile Ala Arg Gln Ser Glu Leu Trp Thr
385                 390                 395                 400

Asp Pro Leu Glu Phe Arg Pro Gly Arg Phe Leu Ile Pro Gly Glu Lys
                405                 410                 415

Pro Asn Val Glu Val Lys Pro Asn Asp Phe Glu Ile Val Pro Phe Gly
                420                 425                 430

Gly Gly Arg Arg Ile Cys Ala Gly Met Ser Leu Gly Leu Arg Met Val
            435                 440                 445

Asn Leu Leu Ile Ala Thr Leu Val Gln Ala Phe Asp Trp Glu Leu Ala
    450                 455                 460

Asn Gly Leu Glu Pro Glu Lys Leu Asn Met Glu Glu Val Phe Gly Ile
465                 470                 475                 480

Ser Leu Gln Arg Val Gln Pro Leu Leu Val His Pro Arg Pro Arg Leu
                485                 490                 495

Ala Arg His Val Tyr Gly Thr Gly
            500

<210> SEQ ID NO 5
<211> LENGTH: 8552
<212> TYPE: DNA
<213> ORGANISM: gCi01-pBluestar
<220> FEATURE:
<221> NAME/KEY: misc_feature
<223> OTHER INFORMATION: gCi01-pBluestar

<400> SEQUENCE: 5
gcggccgcgg atcccgggaa ttctcgatcc agccatgtgt ctagtacaac catacagacg    60
attaaaaaaa aaactttaaa ccacaaaacg ggttttgcaa acgaagaaat tgcctcaaaa   120
catttccata tggagtttag ggacagagtg cgtttgctac attaaacaac tcttttataa   180
aaaaacatag cggtacgaga atgacccact aaccgttcat gtccattggc aaaagttact   240
attgtgagtc ttgtatatac atttaaaaaa aaagaatata tcagttccat aaagggcctg   300
aaacataagt aagaatatat caatgacgtt cggttcggtt tttggtttat ataagagaa   360 cttgatttga aaattacga gaataacaaa tatttggggt gtcattttat aaaatatcaa   420
aattttaaaa ctattttaca aaatgttaac aagtaagttg tttttttttt tttttcaca   480 agcagttgaa acagtttttg ttgaacgtga agttatagct ttacttgaag tttgatattt   540
tggcatcttg acactacatg tcttctagt gtgacccctta tcttacaact atcacatgtc   600
aacggttttg tctgtccttt ggatagtata cggtctttgt tttaggacgt ctcgcatgtg   660
tcctctctat ggtggtgggt tgatcgtatg aatccttagg atcgtagcca tttagaagga   720
tttccgacat ggaatatcaa tcatgtatat gtacgtttat aattctcggc gttgaaccaa   780
tgttgtgtcg aactcccgac atcgttcatt tccaaatgtg ttaaaactgt tgtaaggtgt   840
```

```
gaacaaggta taccatattt tgccaaact tgacaactgc attttttta tcatgttgtc      900 acacacctca tacatttatc attaactggt atgactttcc atccaaactt gacaagctct      960
taaccatttg gcgacatcta aactattcga tagtgactta attcgtaagt taatgcacaa     1020
atgtcgacaa catattccgc gagtcgcatc tggtatggaa cacaaatgga tcaagagggc     1080
taaaacccat gaggttagaa aatttttactt ccaagttcaa gttcatttga tacaagcact     1140
gcaaaatcat tctgcagact aatctaaatc ttattcttcc agagatgata agttagtttg     1200
cagctcggtt tttatgtttt cttgatacgt ttatctgtag atgtgatcga aatgatagta     1260
cacgcgctta ttttttgtag tcgtatcgca tatgttagtt aaaaagtctg aaactaactt     1320
aaaaagtttg tcattttgaa taggtggtag ttgaaaatta ggagtataag tttacaaggg     1380
ttggtgttac ttaacaatct cctaatcttt aagtcattct tttgatttt cggcataaat      1440 atatcgatga caatctccct acataaacgc gattttggtt aataacctga ggtagaaata     1500
tggctggggg tggagaactt agtactatca caacaaaaac aggcgaacat gtggttagga     1560
ggccacgggg caggccagct gggtcaaaaa acaggccgaa accacccatt atcattaccc     1620
gagacagtgc caatacgttg cgggctcatg ccatggaggt tagcccaggg tgtgacattg     1680
ttgagagctt agccactttt gctaggagga acaacaagg gatttgggtg ctaagtgccg      1740
ctggatttgt gagcaatgtt atgttgcgtc aacctggccc atcacaggct ggtacgggtt     1800
ccgggcctat tgtcacactt catggccggt ttgagatttt atctttggtt ggttctgtat     1860
tgccacatcc ggctccgcca ggtgtcactg ggttagccat atatttagtt ggcccgcagg     1920
gccaagtcgt gggtggtgcc attgctggcc cactcatgac atcgggacct gtggtgctca     1980
tggcagccac tttcatgaat gccactttcg ataggttgcc tatcgaaaaa gatgaaatgg     2040
ttgcagccac tactacacac gatcgacatc accattgtgt caatggtgtt tcggatattt     2100
atgggacgac ccaacaaaac atgctttcta acacaaccct ccctcatccc gagatttata     2160
cctggtcaac ggctcgacca ttgtccaagg cataagttat ggaaaagaaa aaataaaaaa     2220
catatagaaa gtaaactttt aaaacttgtg taagcccaaa ttgtattact caagatcggc     2280
aggcgattta cgacctcagt tacgtgttta agcgtttgat atgtaaactt ttacgagcga     2340
aaaatgatca agaaaattta gtcatatgaa gttagaagtc attagattct gtaatgtaat     2400
gtatgtttct ggtatcaaaa gttattatca gtttgtgttt ctaaatcctt aacagaatca     2460
atatgcattc gacttacagt gattaagacg atcatagaag ggattatcgt cacaaaattt     2520
agtcagatac ttatgaactg acaaaatcct ttacagaatc aatatgcatt agacttacag     2580
tgcaaacata tacgccgaga gctaaaagcg acggtgataa gagtagaatc gtaatttcac     2640
agaatcagca gacttcttat aaagaaaaca caactgaaaa tcaagttcac aaactacttc     2700
atttactaat ctttgatgtt caacaagtcg ttggcgaggg catgggtact tcggtaattt     2760
cacacaactc atgaatgttt ttatgaagaa aacacttcca agtataaacc aagttctcaa     2820
actaatatgt tcactaatca atgacgttcg agtaaatcac acctgaatac aatgagccta     2880
gattttacct ggcaattcga attttcaaac cattgaacta atcttttgca ataattctct     2940
tgcaccaaga tcatcgggtg aacgagaggt ccactcctgg taatggcgaa gactaccagt     3000
gaaatctgta aaaagcccgt caaggcgtca actcccattg tgtctatcca gtaattgtat     3060
tccatatatg ggccttcaca gaatttgaaa tgcaagaact ggttttcatt gcgaaatgtg     3120
taagggtgca gctgcaagta ttagtaaaag acgttcggtt tgacttttga ggtcaacaca     3180
tagaaaaatt ctactccaat tttactcgaa gtaatgtgat tttcaggaaa gattacaaag     3240
```

```
aaactcgtaa catattaaat atgggacaat attagtatta agaacttacc cagattcaaa    3300
tcagtttgaa aatttgaaag ttatatataa agataaaatt tgacctctca aggtcaaaca    3360
gagaaatcca actccgttta tacacaacct taacgaaatt ttaagaaaat atcaacgatt    3420
accaaaacag ttctaacatg ttaacacgtg aaacgattc gtctcttgag actaagtaaa     3480
ttatatttac attaatgtgt gattctgaaa aaggtcgtc aaaatatcta ttaaatctaa     3540
tgtacctgta gattatgggc gtgagctcgg gttttgagat tggggaggcgt ttgaatgtag   3600 ttatctttca caggaacaac agtgtctttc catggaccaa taccgacaac atattctttg    3660
atatatttga gtaacgatc tgaagtgatt tctgcatacg tctgcaaatg aaaaagaaat     3720
cagattataa acatccattg caaactatcc ttgcatcgtg tttggatgtt cgttttaagc    3780
gagtatttta tggaataggg agaatcagac aattagttgt aataaaacat gatctttaat    3840
tgtgctacta gtttaagtta taatgataat agaaaacatt tagtcttcgg aaaattatat    3900
aaattaccaa aaatgggttt aactgtttca aaccaaaagt ggcaagatgt caggtcggat    3960
ggattgggta acgggtcaaa atgggttgga ctgaaacatg ttcaaacata gcgcgtaggc    4020
cgtagagatt acaaaaattc tccgttccaa ataaggttaa cagatatgac tatgctgact    4080
ttttaagtgt caaatgcgat tctctttttcc ggtatgcata aaaaactgac gacggacatt   4140
acactatata aaaatttaga aggttataat aaaccaagaa aatataattg tattaaattg    4200
tgtgagttat atgaattaca tagaacctt tatatatggt tgaattacct tgctgaacaa     4260
gaaacctaaa cctattagaa atgtctcaaa aatcctaagc ttcaggaata ccttcccggc    4320
cttagcgacg aggaagatat gctagagtgt atgtgtgact cgttaaaatc atgaactaga    4380 acaagggaa aggaacaatg ttacaatctc aatgattaga taggatataa ctcgataaca     4440
aacctaacca gcagagttag atcaagtggt aagtctttgc ctttgaagac ataggtcgag    4500
ggttcgatcc tcactccatg tggtcggagg tttattggtg aatgcatgct tagctaccgt    4560
tcaaagtaac tttattggtg aatgcatgct tagctaccgt tcaaaatctt caaaaagggt    4620
aattatgtct aatatgccat ctaagttcta accaacccct caaatgttca ttcctataat    4680
tactaaccaa ttcttacgtt gtcaagtaaa taaaatgagc attctaaccc taatctgcac    4740
cttcatcact ggtttgatgt tctatgggtt ggttaatttg cttagccgtc gcgctagccg    4800
tcttcctcca ggtccaaccc catggccaat catcggcaac ctaatgcacc ttggtaaact    4860
tccacatcac tcgctggcgg acttggcgaa aaagtatggt ccgttgatac atgtccgact    4920
agggtccgtt gatgttgtgg tggcctcgtc tgcgtccgtt gctgggcagt ttttaaaggt    4980
gcatgatgcg aattttgcca acaggccacc aaattctgga gctaaacata tggcgtataa    5040
ttatcatgat atggtgtttg cgccgtatgg tccaaggtgg cgaatgcttc gaaagatgtg    5100
ctccatgcat ctgttttctg ccaaagcact cactgatttt cgtcaagttc gacaggtttt    5160
gtactttcac tttcgtcata tatataggga gattagtacg agaacgaaca cttttaaaat    5220 cacttttaa taatcaaaat atcttttttt ttttaaacaa aatcatggaa tcttattcaa     5280
ataacttttc taaccttcta aattttttt aatttttaa tttttttt acttacagtg        5340 attaagataa tcacataaaa tatatagata atcacatgaa atttttgtg attatttagt     5400 tcaaatacat tattatcgat atattttttg tgattatctt aaccaccgta aaaaaaattc    5460
aaaaataaaa taaatctga gaaggttaaa aaagttatat aaataagatt ttccgatttt    5520
gttttcaaca ataaaataaa atttcagaac gtaataaaaa ttgattttt gttaacgaga     5580
```

```
gtttgtaaca atagacggtc aacgaaaat gtgtattatc tggtggtatc accatcggat    5640
tatgccaagc atgcataaaa aaacaaaatc gtaactacag gaggaggtaa cgatactcac    5700
gcgcgttttg gccaggactg gacaatcggc agtgaaacta gatcaacaac ttaacgtgtg    5760
cttcgcaaac acattatccc gaatgatgtt agacaggaga gtatttggag acggtgatcc    5820
aaaggcggac gactacaagg atatggtggt tgagttgatg actttggccg gacaattcaa    5880
catcggtgac tacattcctt ggcttgactt gcttgaccta caaggcattg tcaaaaggat    5940
gaagaaagtt cattctcaat tcgattcgtt ccttgacacc atcattgatg aacatactat    6000
tggcacgggc cgtcatgttg acatgttaag cacaatgatt tcactcaaag ataatgccga    6060
tggagaggga gggaagcttt cgttcatcga gatcaaagct cttctactgg tgcgcgtaat    6120
acatagtagt caacttttt ttttttctgg taatgactct ttgagcaggt aaaatgtccc    6180
caacaggaat caaacttggt acctatcatt tttgggaaaa attttaaaag tactagcttt    6240
ttcaaaaaga ttatgaaaag tatctgtttt tctggacgat tgttaaatct accccaaacg    6300
catgtcttat atgcgttccc ttaatcaaac gttgagggtg cgcatatggt acatgcatac    6360
cctccaaagg agttcccatg cacgttgagg gtgcacatat acacatgcgc accctcttcg    6420
tggtttgcca ccaaggcaaa tcctggagga cagtcaacct ttttgatata agttcagatc    6480
taactctagg ctaatactgt tgatgtttca gaacttgttc tcagcgggaa cggacacgtc    6540
atctagtacc gtggaatggg gaatagcgga actcattcgc cacccacagc taatgaaaca    6600
agcgcaagaa gaaatggaca ttgtagttgg aaaaaccgg cttgtaacag aaatggacat    6660
aagccaacta acattccttc aagccattgt gaaagaaacg tttaggctac accccgcgac    6720
gccactttcc ctgccaagga ttgcatcaga aagctgtgag gtcaaggggt atcatgttcc    6780
taagggatcg atactctttg ttaacgtgtg ggccattgct cgacaatcag aattgtggac    6840
cgacccactt gaatttcggc ctggtcgttt cctaatccca ggagaaaaac ctaatgttga    6900
agtgaagcca aatgatttcg aaattgtacc attcggggga ggacgaagga tttgtgcagg    6960
tatgagcctc ggattgagaa tggtcaattt gcttattgca acattggttc aagcctttga    7020
ttgggaattg gctaatgggt tagagccaga aaagcttaac atggaagaag tgtttgggat    7080
tagccttcaa agggttcaac ccttgttggt gcacccgagg ccaaggttag cccgtcacgt    7140
atacggaacg ggttaaggaa ataaactgtc tgtttgtaag atgaatctgt ttgaatttat    7200
gtattaaata gttatgctaa gaactatttt tacaaataaa agtatattgg tttgattgtt    7260
ctcgcttagc ctttgctaaa tcttagatag atgagttgta taacacatca tcattaactc    7320
acatcacgtg gtaacgattt gttttttgagt taaaatttt aaagaaagga aagaaagaga    7380
aagtaaatat aaaaaaattt gtgttcccga gaagtttttt acgaaggaag aggggagaaa    7440
gagagagaat tttagagaaa ttttgagtat tttacaacaa aaatcatcct ctcatttttg    7500
ggatgatttg gaggatcttt tttctttctt ttccttcgtc cacttcacct cccttctttt    7560
ccaaaaaaat ctcggaaaca tagcgtaatg ataaacaaaa accaataaaa atgagcagga    7620
gcaaacccta gaaggacgaa atcttgaaaa tttattctaa gattttttaaa aaaaacttgg    7680
cagttggaaa gggcggcgga tatcagtagg tagttgtgtc acaacgacca gggcggtgtg    7740
tcaagaaacc ttgttttgag ttgtgtctat atttaaggct ccaaaatctc cctcgacttc    7800
aaagtgtaca tagaactgcg ttcaaagtga ccgtaggact gcttgtgagt aggagataac    7860
tacaaaatta aacttagtta ggaattagta tgtccgacca aaagattgtg atggtttaga    7920
attaagagac aattacatat attttcaatt aaaactctat aataaaatat ttttcaatca    7980
```

```
aatttttaaaa taatatatat atatttattt taaaagtata taataatata tttatccaat      8040
caaattttaa aataacatat atatatatat tttaaaattt taaattatat atttatccat       8100
ttctatcaat tataataaaa aaataactat tataccttt ttgataaaac aaaataaaca        8160
tatttaacaa atttattat ataaacttca ataaaatata aatatatga aataaacaga        8220 aatcgtgtta tcgcttactt gaatcaaata ataagttgca gaagataaaa aaaaaattag       8280
actttgaaaa ataaaataaa aataatata tggttataaa tactataatt tatcaaaaat       8340
actatatttt atcaaaatcc aaaacaaata gttttttgt tatgaaaaaa aaaatctcta       8400
cacaaacaca ttaaaattt ataatttaat ttcaaatctc aattaattat ttgagaagat       8460
tcgttcaata tatttgttaa taaagtggac aataagaatt tatttgcttc aaataaacga      8520
caacatgatt tttgttaatt tcatatattt tg                                    8552

<210> SEQ ID NO 6
<211> LENGTH: 5638
<212> TYPE: DNA
<213> ORGANISM: Senecio cruentus
<220> FEATURE:
<221> NAME/KEY: misc_feature
<223> OTHER INFORMATION: PvuI-EcoRV fragment from gCi01-pBluestar
<220> FEATURE:
<221> NAME/KEY: exon
<222> LOCATION: (2652)..(3092)
<220> FEATURE:
<221> NAME/KEY: exon
<222> LOCATION: (3618)..(4046)
<220> FEATURE:
<221> NAME/KEY: exon
<222> LOCATION: (4449)..(5090)

<400> SEQUENCE: 6
cgacatcacc attgtgtcaa tggtgtttcg gatatttatg ggacgaccca acaaaacatg        60
ctttctaaca caaccctccc tcatcccgag atttatacct ggtcaacggc tcgaccattg       120
tccaaggcat aagttatgga aagaaaaaa taaaaaacat atagaaagta aacttttaaa       180
acttgtgtaa gcccaaattg tattactcaa gatcggcagg cgatttacga cctcagttac      240
gtgtttaagc gtttgatatg taaacttta cgagcgaaaa atgatcaaga aaatttagtc       300
atatgaagtt agaagtcatt agattctgta atgtaatgta tgtttctggt atcaaaagtt      360
attatcagtt tgtgtttcta aatccttaac agaatcaata tgcattcgac ttacagtgat      420
taagacgatc atagaaggga ttatcgtcac aaaatttagt cagatactta tgaactgaca      480 aaatcctttta cagaatcaat atgcattaga cttacagtgc aaacatatac gccgagagct     540
aaaagcgacg gtgataagag tagaatcgta atttcacaga atcagcagac ttcttataaa      600
gaaaacacaa ctagaaatca agttcacaaa ctacttcatt tactaatctt tgatgttcaa      660
caagtcgttg gcgagggcat gggtacttcg gtaatttcac acaactcatg aatgttttta      720
tgaagaaaac acttccaagt ataaaccaag ttctcaaact aatatgttca ctaatcaatg      780
acgttcgagt aaatcacacc tgaatacaat gagcctagat tttacctggc aattcgaatt      840
ttcaaaccat tgaactaatc tttttgcaata attctcttgc accaagatca tcgggtgaac      900
gagaggtcca ctcctggtaa tggcgaagac taccagtgaa atctgtaaaa agcccgtcaa      960
ggcgtcaact cccattgtgt ctatccagta attgtattcc atatatgggc cttcacagaa     1020
tttgaaatgc aagaactggt tttcattgcg aaatgtgtaa gggtgcagct gcaagtatta     1080
gtaaaagacg ttcggtttga cttttgaggt caacacatag aaaaattcta ctccaatttt    1140
```

```
actcgaagta atgtgatttt caggaaagat tacaaagaaa ctcgtaacat attaaatatg    1200
ggacaatatt agtattaaga acttacccag attcaaatca gtttgaaaat ttgaaagtta    1260
tatataaaga taaaatttga cctctcaagg tcaaacagag aaatccaact ccgtttatac    1320
acaaccttaa cgaaatttta agaaaatatc aacgattacc aaaacagttc taacatgtta    1380
acacgtggaa acgattcgtc tcttgagact aagtaaatta tatttacatt aatgtgtgat    1440
tctgaaaaaa ggtcgtcaaa atatctatta aatctaatgt acctgtagat tatgggcgtg    1500
agctcgggtt ttgagattgg gaggcgtttg aatgtagtta tctttcacag gaacaacagt    1560
gtctttccat ggaccaatac cgacaacata ttctttgata tatttgaagt aacgatctga    1620
agtgatttct gcatacgtct gcaaatgaaa aagaaatcag attataaaca tccattgcaa    1680
actatccttg catcgtgttt ggatgttcgt tttaagcgag tatttatgg aataggaga     1740
atcagacaat tagttgtaat aaaacatgat ctttaattgt gctactagtt taagttataa    1800
tgataataga aaacatttag tcttcggaaa attatataaa ttaccaaaaa tgggtttaac    1860
tgtttcaaac caaaagtggc aagatgtcag gtcggatgga ttgggtaacg ggtcaaaatg    1920
ggttggactg aaacatgttc aaacatagcg cgtaggccgt agagattaca aaaattctcc    1980
gttccaaata aggttaacag atatgactat gctgactttt taagtgtcaa atgcgattct    2040
cttttccggt atgcataaaa aactgacgac ggacattaca ctatataaaa atttagaagg    2100
ttataataaa ccaagaaaat ataattgtat taaattgtgt gagttatatg aattacatag    2160
aaccttttat atatggttga attccttgc tgaacaagaa acctaaacct attagaaatg      2220
tctcaaaaat cctaagcttc aggaatacct tcccggcctt agcgacgagg aagatatgct    2280
agagtgtatg tgtgactcgt taaaatcatg aactagaaca aagggaaagg aacaatgtta    2340
caatctcaat gattagatag gatataactc gataacaaac ctaaccagca gagttagatc    2400
aagtggtaag tctttgcctt tgaagacata ggtcgagggt tcgatcctca ctccatgtgg    2460
tcggaggttt attggtgaat gcatgcttag ctaccgttca aagtaacttt attggtgaat    2520
gcatgcttag ctaccgttca aaatcttcaa aaagggtaat tatgtctaat atgccatcta    2580
agttctaacc aacccttcaa atgttcattc ctataattac taaccaattc ttacgttgtc    2640
aagtaaataa a atg agc att cta acc cta atc tgc acc ttc atc act ggt    2690
             Met Ser Ile Leu Thr Leu Ile Cys Thr Phe Ile Thr Gly
              1               5                  10
ttg atg ttc tat ggg ttg gtt aat ttg ctt agc cgt cgc gct agc cgt     2738
Leu Met Phe Tyr Gly Leu Val Asn Leu Leu Ser Arg Arg Ala Ser Arg
    15                  20                  25
ctt cct cca ggt cca acc cca tgg cca atc atc ggc aac cta atg cac    2786
Leu Pro Pro Gly Pro Thr Pro Trp Pro Ile Ile Gly Asn Leu Met His
30                  35                  40                  45
ctt ggt aaa ctt cca cat cac tcg ctg gcg gac ttg gcg aaa aag tat    2834
Leu Gly Lys Leu Pro His His Ser Leu Ala Asp Leu Ala Lys Lys Tyr
                50                  55                  60
ggt ccg ttg ata cat gtc cga cta ggg tcc gtt gat gtt gtg gtg gcc    2882
Gly Pro Leu Ile His Val Arg Leu Gly Ser Val Asp Val Val Val Ala
                65                  70                  75
tcg tct gcg tcc gtt gct ggg cag ttt tta aag gtg cat gat gcg aat    2930
Ser Ser Ala Ser Val Ala Gly Gln Phe Leu Lys Val His Asp Ala Asn
            80                  85                  90
ttt gcc aac agg cca cca aat tct gga gct aaa cat atg gcg tat aat    2978
Phe Ala Asn Arg Pro Pro Asn Ser Gly Ala Lys His Met Ala Tyr Asn
        95                  100                 105
tat cat gat atg gtg ttt gcg ccg tat ggt cca agg tgg cga atg ctt    3026
```

-continued

```
Tyr His Asp Met Val Phe Ala Pro Tyr Gly Pro Arg Trp Arg Met Leu
110             115                 120                 125 cga aag atg tgc tcc atg cat ctg ttt tct gcc aaa gca ctc act gat    3074
Arg Lys Met Cys Ser Met His Leu Phe Ser Ala Lys Ala Leu Thr Asp
                130                 135                 140 ttt cgt caa gtt cga cag gttttgtact ttcactttcg tcatatatat           3122
Phe Arg Gln Val Arg Gln
                145 agggagatta gtacgagaac gaacactttt aaaatcactt tttaataatc aaaatatctt  3182 ttttttttta aacaaaatca tggaatctta ttcaataaac ttttctaacc ttctaaattt  3242 tttttaattt ttttaattttt tttttactta cagtgattaa gataatcaca taaaatatat 3302 agataatcac atgaaatttt ttgtgattat ttagttcaaa tacattatta tcgatatatt  3362 ttttgtgatt atcttaacca ccgtaaaaaa aattcaaaaa taaataaaaa tctgagaagg  3422 ttaaaaaagt tatataaata agattttccg attttgtttt caacaataaa ataaaatttc  3482 agaacgtaat aaaaattgat ttttttgttaa cgagagtttg taacaataga cggtcaacgg 3542 aaaatgtgta ttatctggtg gtatcaccat cggattatgc caagcatgca taaaaaaaca  3602 aaatcgtaac tacag gag gag gta acg ata ctc acg cgc gtt ttg gcc agg  3653
              Glu Glu Val Thr Ile Leu Thr Arg Val Leu Ala Arg
                                150                 155 act gga caa tcg gca gtg aaa cta gat caa caa ctt aac gtg tgc ttc    3701
Thr Gly Gln Ser Ala Val Lys Leu Asp Gln Gln Leu Asn Val Cys Phe
160                 165                 170                 175 gca aac aca tta tcc cga atg atg tta gac agg aga gta ttt gga gac    3749
Ala Asn Thr Leu Ser Arg Met Met Leu Asp Arg Arg Val Phe Gly Asp
                180                 185                 190 ggt gat cca aag gcg gac gac tac aag gat atg gtg gtt gag ttg atg    3797
Gly Asp Pro Lys Ala Asp Asp Tyr Lys Asp Met Val Val Glu Leu Met
                195                 200                 205 act ttg gcc gga caa ttc aac atc ggt gac tac att cct tgg ctt gac    3845
Thr Leu Ala Gly Gln Phe Asn Ile Gly Asp Tyr Ile Pro Trp Leu Asp
            210                 215                 220 ttg ctt gac cta caa ggc att gtc aaa agg atg aag aaa gtt cat tct    3893
Leu Leu Asp Leu Gln Gly Ile Val Lys Arg Met Lys Lys Val His Ser
225                 230                 235 caa ttc gat tcg ttc ctt gac acc atc att gat gaa cat act att ggc    3941
Gln Phe Asp Ser Phe Leu Asp Thr Ile Ile Asp Glu His Thr Ile Gly
240                 245                 250                 255 acg ggc cgt cat gtt gac atg tta agc aca atg att tca ctc aaa gat    3989
Thr Gly Arg His Val Asp Met Leu Ser Thr Met Ile Ser Leu Lys Asp
                260                 265                 270 aat gcc gat gga gag gga ggg aag ctt tcg ttc atc gag atc aaa gct    4037
Asn Ala Asp Gly Glu Gly Gly Lys Leu Ser Phe Ile Glu Ile Lys Ala
                275                 280                 285 ctt cta ctg gtgcgcgtaa tacatagtag tcaactttt tttttttctg              4086
Leu Leu Leu
        290 gtaatgactc tttgagcagg taaaatgtcc ccaacaggaa tcaaacttgg tacctatcat  4146 ttttgggaaa aattttaaaa gtactagctt tttcaaaaag attatgaaaa gtatctgttt  4206 ttctggacga ttgttaaatc taccccaaac gcatgtctta tatgcgttcc cttaatcaaa  4266 cgttgagggt gcgcatatgg tacatgcata ccctccaaag gagttcccat gcacgttgag  4326 ggtgcacata tacacatgcg cacccctcttc gtggtttgcc accaaggcaa atcctggagg 4386 acagtcaacc tttttgatat aagttcagat ctaactctag gctaatactg ttgatgtttc  4446
```

```
ag aac ttg ttc tca gcg gga acg gac acg tca tct agt acc gtg gaa    4493
   Asn Leu Phe Ser Ala Gly Thr Asp Thr Ser Ser Ser Thr Val Glu
               295                 300                 305 tgg gga ata gcg gaa ctc att cgc cac cca cag cta atg aaa caa gcg    4541
Trp Gly Ile Ala Glu Leu Ile Arg His Pro Gln Leu Met Lys Gln Ala
                310                 315                 320 caa gaa gaa atg gac att gta gtt gga aaa aac cgg ctt gta aca gaa    4589
Gln Glu Glu Met Asp Ile Val Val Gly Lys Asn Arg Leu Val Thr Glu
            325                 330                 335 atg gac ata agc caa cta aca ttc ctt caa gcc att gtg aaa gaa acg    4637
Met Asp Ile Ser Gln Leu Thr Phe Leu Gln Ala Ile Val Lys Glu Thr
            340                 345                 350 ttt agg cta cac ccc gcg acg cca ctt tcc ctg cca agg att gca tca    4685
Phe Arg Leu His Pro Ala Thr Pro Leu Ser Leu Pro Arg Ile Ala Ser
            355                 360                 365 gaa agc tgt gag gtc aag ggg tat cat gtt cct aag gga tcg ata ctc    4733
Glu Ser Cys Glu Val Lys Gly Tyr His Val Pro Lys Gly Ser Ile Leu
370                 375                 380                 385 ttt gtt aac gtg tgg gcc att gct cga caa tca gaa ttg tgg acc gac    4781
Phe Val Asn Val Trp Ala Ile Ala Arg Gln Ser Glu Leu Trp Thr Asp
                390                 395                 400 cca ctt gaa ttt cgg cct ggt cgt ttc cta atc cca gga gaa aaa cct    4829
Pro Leu Glu Phe Arg Pro Gly Arg Phe Leu Ile Pro Gly Glu Lys Pro
                405                 410                 415 aat gtt gaa gtg aag cca aat gat ttc gaa att gta cca ttc ggg gga    4877
Asn Val Glu Val Lys Pro Asn Asp Phe Glu Ile Val Pro Phe Gly Gly
            420                 425                 430 gga cga agg att tgt gca ggt atg agc ctc gga ttg aga atg gtc aat    4925
Gly Arg Arg Ile Cys Ala Gly Met Ser Leu Gly Leu Arg Met Val Asn
435                 440                 445 ttg ctt att gca aca ttg gtt caa gcc ttt gat tgg gaa ttg gct aat    4973
Leu Leu Ile Ala Thr Leu Val Gln Ala Phe Asp Trp Glu Leu Ala Asn
450                 455                 460                 465 ggg tta gag cca gaa aag ctt aac atg gaa gaa gtg ttt ggg att agc    5021
Gly Leu Glu Pro Glu Lys Leu Asn Met Glu Glu Val Phe Gly Ile Ser
                470                 475                 480 ctt caa agg gtt caa ccc ttg ttg gtg cac ccg agg cca agg tta gcc    5069
Leu Gln Arg Val Gln Pro Leu Leu Val His Pro Arg Pro Arg Leu Ala
            485                 490                 495 cgt cac gta tac gga acg ggt taaggaaata aactgtctgt ttgtaagatg       5120
Arg His Val Tyr Gly Thr Gly
            500 aatctgtttg aatttatgta ttaaatagtt atgctaagaa ctattttac aaataaaagt   5180 atattggttt gattgttctc gcttagcctt tgctaaatct tagatagatg agttgtataa  5240 cacatcatca ttaactcaca tcacgtggta acgatttgtt tttgagttaa aattttaaa   5300 gaaaggaaag aaagagaaag taaatataaa aaaatttgtg ttcccgagaa gtttttacg   5360 aaggaagagg ggagaaagag agagaatttt agagaaattt tgagtatttt acaacaaaaa  5420 tcatcctctc attttggga tgatttggag gatctttttt ctttcttttc cttcgtccac   5480 ttcacctccc tttctttcca aaaaatctc ggaaacatag cgtaatgata aacaaaaacc   5540 aataaaaatg agcaggagca aaccctagaa ggacgaaatc ttgaaaattt attctaagat  5600 ttttaaaaaa aacttggcag ttggaaaggg cggcggat                          5638

<210> SEQ ID NO 7
<211> LENGTH: 20
<212> TYPE: DNA
<213> ORGANISM: Artificial
```

<220> FEATURE:
<223> OTHER INFORMATION: Foward primer Ci5a18F1

<400> SEQUENCE: 7
catctgtttt ctgccaaagc                                                    20

<210> SEQ ID NO 8
<211> LENGTH: 19
<212> TYPE: DNA
<213> ORGANISM: Artificial
<220> FEATURE:
<223> OTHER INFORMATION: Reverse primer Ci5a18R1

<400> SEQUENCE: 8
ggattaggaa acgaccagg                                                     19

<210> SEQ ID NO 9
<211> LENGTH: 2651
<212> TYPE: DNA
<213> ORGANISM: Senecio cruentus
<220> FEATURE:
<221> NAME/KEY: misc_feature
<223> OTHER INFORMATION: Petal specific promoter derived from cinerria

<400> SEQUENCE: 9
cgacatcacc attgtgtcaa tggtgtttcg gatatttatg ggacgaccca acaaaacatg      60
ctttctaaca caaccctccc tcatcccgag atttatacct ggtcaacggc tcgaccattg     120
tccaaggcat aagttatgga aagaaaaaa taaaaacat atagaaagta aacttttaaa      180
acttgtgtaa gcccaaattg tattactcaa gatcggcagg cgatttacga cctcagttac    240
gtgtttaagc gtttgatatg taaacttttta cgagcgaaaa atgatcaaga aaatttagtc   300
atatgaagtt agaagtcatt agattctgta atgtaatgta tgtttctggt atcaaaagtt    360
attatcagtt tgtgtttcta aatccttaac agaatcaata tgcattcgac ttacagtgat    420
taagacgatc atagaaggga ttatcgtcac aaaatttagt cagatactta tgaactgaca    480
aaatccttta cagaatcaat atgcattaga cttacagtgc aaacatatac gccgagagct    540
aaaagcgacg gtgataagag tagaatcgta atttcacaga atcagcagac ttcttataaa    600
gaaaacacaa ctagaaatca agttcacaaa ctacttcatt tactaatctt tgatgttcaa    660
caagtcgttg gcgagggcat gggtacttcg gtaattcac acaactcatg aatgttttta    720
tgaagaaaac acttccaagt ataaaccaag ttctcaaact aatatgttca ctaatcaatg    780
acgttcgagt aaatcacacc tgaatacaat gagcctagat tttacctggc aattcgaatt    840
ttcaaaccat tgaactaatc ttttgcaata attctcttgc accaagatca tcgggtgaac    900
gagaggtcca ctcctggtaa tggcgaagac taccagtgaa atctgtaaaa agcccgtcaa    960
ggcgtcaact cccattgtgt ctatccagta attgtattcc atatatgggc cttcacagaa   1020
tttgaaatgc aagaactggt tttcattgcg aaatgtgtaa gggtgcagct gcaagtatta   1080
gtaaaagacg ttcggtttga cttttgaggt caacacatag aaaaattcta ctccaatttt   1140
actcgaagta atgtgatttt caggaaagat tacaagaaa ctcgtaacat attaaatatg    1200
ggacaatatt agtattaaga acttacccag attcaaatca gtttgaaaat ttgaaagtta   1260
tatataaaga taaaatttga cctctcaagg tcaaacagag aaatccaact ccgtttatac   1320
acaaccttaa cgaaatttta agaaaatatc aacgattacc aaaacagttc taacatgtta   1380
acacgtggaa acgattcgtc tcttgagact aagtaaatta tatttacatt aatgtgtgat   1440
tctgaaaaaa ggtcgtcaaa atatctatta aatctaatgt acctgtagat tatgggcgtg   1500

```
agctcgggtt ttgagattgg gaggcgtttg aatgtagtta tctttcacag gaacaacagt    1560
gtctttccat ggaccaatac cgacaacata ttctttgata tatttgaagt aacgatctga    1620
agtgatttct gcatacgtct gcaaatgaaa agaaatcag attataaaca tccattgcaa     1680
actatccttg catcgtgttt ggatgttcgt tttaagcgag tattttatgg aatagggaga    1740
atcagacaat tagttgtaat aaaacatgat ctttaattgt gctactagtt taagttataa    1800
tgataataga aaacatttag tcttcggaaa attatataaa ttaccaaaaa tgggtttaac    1860
tgtttcaaac caaaagtggc aagatgtcag gtcggatgga ttgggtaacg ggtcaaaatg    1920
ggttggactg aaacatgttc aaacatagcg cgtaggccgt agagattaca aaaattctcc    1980
gttccaaata aggttaacag atatgactat gctgactttt taagtgtcaa atgcgattct    2040
cttttccggt atgcataaaa aactgacgac ggacattaca ctatataaaa atttagaagg    2100
ttataataaa ccaagaaaat ataattgtat taaattgtgt gagttatatg aattacatag    2160 aacctttat atatggttga attaccttgc tgaacaagaa acctaaacct attagaaatg      2220
tctcaaaaat cctaagcttc aggaatacct tcccggcctt agcgacgagg aagatatgct    2280
agagtgtatg tgtgactcgt taaaatcatg aactagaaca aagggaaagg aacaatgtta    2340
caatctcaat gattagatag gatataactc gataacaaac ctaaccagca gagttagatc    2400
aagtggtaag tctttgcctt tgaagacata ggtcgagggt tcgatcctca ctccatgtgg    2460
tcggaggttt attggtgaat gcatgcttag ctaccgttca aagtaacttt attggtgaat    2520
gcatgcttag ctaccgttca aaatcttcaa aaagggtaat tatgtctaat atgccatcta    2580
agttctaacc aacccttcaa atgttcattc ctataattac taaccaattc ttacgttgtc    2640
aagtaaataa a                                                        2651

<210> SEQ ID NO 10
<211> LENGTH: 548
<212> TYPE: DNA
<213> ORGANISM: Senecio cruentus
<220> FEATURE:
<221> NAME/KEY: misc_feature
<223> OTHER INFORMATION: Petal specific terminator derived from
      cineraria

<400> SEQUENCE: 10
taaggaaata aactgtctgt ttgtaagatg aatctgtttg aatttatgta ttaaatagtt      60
atgctaagaa ctattttac aaataaaagt atattggttt gattgttctc gcttagcctt     120
tgctaaatct tagatagatg agttgtataa cacatcatca ttaactcaca tcacgtggta    180
acgatttgtt tttgagttaa aattttaaa gaaaggaaag aaagagaaag taaatataaa     240
aaaatttgtg ttcccgagaa gttttttacg aaggaagagg ggagaaagag agagaatttt    300
agagaaattt tgagtatttt acaacaaaaa tcatcctctc attttggga tgatttggag      360 gatctttttt ctttctttc cttcgtccac ttcacctccc tttctttcca aaaaatctc      420 ggaaacatag cgtaatgata aacaaaaacc aataaaaatg agcaggagca aaccctagaa    480
ggacgaaatc ttgaaaattt attctaagat ttttaaaaaa aacttggcag ttggaaaggg    540
cggcggat                                                             548

<210> SEQ ID NO 11
<211> LENGTH: 35
<212> TYPE: DNA
<213> ORGANISM: Artificial
<220> FEATURE:
```

```
<223> OTHER INFORMATION: CinF 5146-5170S promoter

<400> SEQUENCE: 11
gcatcccggg agttcgacag gttttgtact ttcac                              35

<210> SEQ ID NO 12
<211> LENGTH: 35
<212> TYPE: DNA
<213> ORGANISM: Artificial
<220> FEATURE:
<223> OTHER INFORMATION: CinR 5670-5690RV promoter

<400> SEQUENCE: 12
gcatgtcgac gatatcacct cctcctgtag ttacg                              35

<210> SEQ ID NO 13
<211> LENGTH: 23
<212> TYPE: DNA
<213> ORGANISM: Artificial
<220> FEATURE:
<223> OTHER INFORMATION: CinF 3113-3128RV promoter

<400> SEQUENCE: 13
gaaatgtgta agggtgcagc tgc                                           23

<210> SEQ ID NO 14
<211> LENGTH: 42
<212> TYPE: DNA
<213> ORGANISM: Artificial
<220> FEATURE:
<223> OTHER INFORMATION: CinR 4694-4714RI promoter

<400> SEQUENCE: 14
tttatttact tgacaacgta agaattcgtt agtaattata gg                      42
```

CINERARIA-DERIVED CHROMOSOMAL DNA INVOLVED IN SYNTHESIS OF FLAVONOID, AND USE THEREOF

CROSS REFERENCE TO RELATED APPLICATIONS

This application is the National Stage of International Application No. PCT/JP2009/068736 filed Oct. 26, 2009, and claims benefit of Japanese Patent Application No. 2008-276029, filed Oct. 27, 2008, which are herein incorporated by reference in their entirety.

TECHNICAL FIELD

The present invention relates to a novel *cineraria*-derived polynucleotide containing a transcription control region of flavonoid 3',5'-hydroxylase (F3'5'H), a 5'-untranslated region, an exon, an intron, a 3'-untranslated region and a sequence required for terminating transcription, a novel gene construct containing the polynucleotide, and a genetically modified plant containing that construct.

BACKGROUND ART

In roses, as shown in FIG. 1, the number of hydroxyl groups of ring B (upper right) has a considerable effect on anthocyanidin (flower color), and when the number of hydroxyl groups is three, flower color frequently changes from blue to violet. In fact, many flowers ranging from blue to violet in color contain anthocyanin derived from delphinidin.

Enzymes that govern B ring hydroxylation consist of flavonoid 3'-hydroxylase (F3'H) and flavonoid 3',5'-hydroxylase (F3'5'H), and the genes of both enzymes are acquired from numerous plants including petunias. Based on a comparison of amino acid sequences, F3'H and F3'5'H belong sub-families classified into CYP75B and CYP75A, respectively, of the cytochrome P450 super family (refer to Non-Patent Document 1). Recently, enzymes having F3'5'H activity of aster and osteospermum (which are both members of the aster family) have been reported to belong to the CYP75B sub-family. On the other hand, these plants also have enzymes belonging to the CPY75B sub-family that have F3'H activity. Thus, plants belonging to the aster family are presumed to have genes belonging to the CYP75B that overlap, and acquired a function for encoding enzymes having F3'5'H activity (refer to Non-Patent Document 2).

However, a protein designated as F3'5'H of *cineraria* (Pericallis cruenta or Senecio cruentus), which is also a member of the aster family, is registered as Accession No. AAX1988 of the protein database of the National Center for Biotechnology information. Although examples of measuring the activity of this protein in yeast have been reported (refer to Non-Patent Document 2), since results of measuring the activity of this protein in plants have not been reported, its function is unclear.

Since plants such as roses and carnations are unable to synthesize delphinidin due to the absence of F3'5'H gene, there are no varieties having a violet to blue flower color. It would be industrially useful if it were possible to produce varieties having violet to blue color. Recently, varieties having violet to blue color, which were unable to be obtained with conventional cross-breeding, have been developed by expressing F3'5'H gene in roses and carnations by utilizing genetic recombination techniques (refer to Non-Patent Document 1 and Non-Patent Document 3). In addition, examples have also been reported of changing flower color using genetic recombination techniques (refer to Non-Patent Document 4).

For example, several plants are unable to produce bright red and orange flowers as a result of not producing pelargonidin. Since the dihydroflavonol 4-reductase of flowers such as petunias is unable to reduce dihydrokaempferol, they do not produce pelargonidin. On the other hand, it has been demonstrated experimentally in vitro that inhibiting expression of flavonoid 3'-hydroxylase (F3'H) gene in chrysanthemums results in accumulation of pelargonidin (refer to Non-Patent Document 5). However, there are no chrysanthemums currently known that actually accumulate pelargonidin as a primary anthocyanidin.

In these reports, an exogenous gene is linked to a constitutive promoter or pedal-specific promoter in order to express the exogenous gene in petals. A promoter of a constitutive gene involved in flavonoid biosynthesis is frequently used for the petal-specific promoter. For example, a promoter such as that derived from chalcone synthase present in snapdragons is used in carnations to accumulate delphinidin (refer to Patent Document 1 and Patent Document 2).

However, it is difficult to predict the degree to which a target gene is expressed in a certain plant when using a certain promoter. In addition, a nucleotide sequence required to terminate transcription referred to as a terminator is frequently used in addition to a promoter to express a target gene. Although the gene terminators of nopaline synthase, mannopine synthase and octopine synthase derived from *Agrobacterium* are frequently used, it is not easy to predict in advance which terminator should be used to allow a target gene to function properly. In addition, although there are also cases in which chromosomal genes of plant genes (translation sequence regions or terminator regions containing promoters and introns) are allowed to function by inserting directly into a plant (refer to, for example, Non-Patent Document 2), in such cases as well, it is difficult to predict whether or not the inserted gene will actually function.

Moreover, plants frequently exhibit a high degree of polyploidy. Cultivated roses are tetraploids, cultivated chrysanthemums are hexaploids, and *cineraria* are octoploids. Thus, genes of enzymes such as F3'5'H involved in flavonoid synthesis are predicted to be present in these plants in at least the number of the polyploidy. Even if all of these are not transcribed and function, since the plant is able to demonstrate F3'5'H activity, it is not easy to isolate a promoter that is actually able to function from these plants.

A method involving transcription of double-stranded RNA (to also be referred to as RNAi) is generally widely used to inhibit gene expression.

In red petunias that produce cyanidin, expression of F3'H gene is inhibited by transcribing its double-stranded RNA, while at the same time, petunias having an orange color are obtained by causing pelargonidin to accumulate by expressing DFR enzyme gene derived from roses (refer to Non-Patent Document 6).

In addition, in chrysanthemums as well, there are examples of inhibiting expression of F3'H gene, causing excess expression of pansy F3'5'H gene and accumulating delphinidin by transcribing its double-stranded RNA (pCGP3429, refer to Patent Document 3).

When transcribing double-stranded RNA, a cDNA-derived sequence (such as an F3'H cDNA sequence) or an unrelated sequence (such as an *E. coli*-derived GUS sequence) can be inserted between sequences generating an inverted repeat sequence. Although inhibition efficiency of a target gene has been reported to be increased when an intron sequence is inserted therein (refer to Non-Patent Document 7), since there are numerous types of intron sequences, it is not easy even for a person skilled in the art to predict which specific intron sequence should be used.

PRIOR ART DOCUMENTS

Patent Documents

Patent Document 1: Published Japanese Translation of PCT Publication No. H8-511683
Patent Document 2: Published Japanese Translation of PCT Publication No. H11-505116
Patent Document 3: PCT/AU2008/001694

Non-Patent Documents

Non-Patent Document 1: Phytochemistry Rev. (2006), 5, 283-291
Non-Patent Document 2: Plant Mol. Biol. (2006), 61, 365-381
Non-Patent Document 3: Plant Cell Physiol. (2007), 48, 1589-1600
Non-Patent Document 4: Curr. Opin. Biotechnol. (2008), 19, 190-197
Non-Patent Document 5: Phytochemistry (1993), 35, 145-150
Non-Patent Document 6: Plant Biotechnology (2004), 21, 377-386
Non-Patent Document 7: Nature (2000), 407, 319-320

SUMMARY OF THE INVENTION

Problems to be Solved by the Invention

An object of the present invention is to provide a novel *cineraria*-derived polynucleotide able to function as a promoter of a coding region of flavonoid 3',5'-hydroxylase (F3'5'H) for use as a tool for changing flower color, and to provide a novel F3'5'H gene construct that contains that polynucleotide.

In addition, an object of the present invention is to provide a novel *cineraria*-derived polynucleotide that contains a transcription control region of flavonoid 3',5'-hydroxylase (F3'5'H) gene, a 5'-untranslated region, an exon, an intron, a 3'-untranslated region and a sequence required for terminating transcription, and to provide a novel gene construct containing that polynucleotide and a genetically modified plant containing that construct.

Means for Solving the Problems

As a result of repeatedly conducting experiments and extensive research to solve the aforementioned problems, the inventors of the present invention acquired a gene construct able to actually function from a chromosomal clone of *cineraria*, and expressed that construct in petunias and chrysanthemums, thereby leading to completion of the present invention.

More specifically, the present invention provides the following [1] to [14]:

[1] a *cineraria*-derived petal-specific promoter selected from the group consisting of:
(1) all or a portion of polynucleotide having the nucleotide sequence indicated in SEQ ID NO: 9, and
(2) a polynucleotide that hybridizes with all or a portion of the polynucleotide having the nucleotide sequence indicated in SEQ ID NO: 9 under stringent conditions and functions as a promoter of a coding region of flavonoid 3',5'-hydroxylase (F3'5'H).

[2] An F3'5'H gene construct comprising the *cineraria*-derived petal-specific promoter described in [1] above.

[3] The F3'5'H gene construct described in [2] above, further comprising a *cineraria*-derived terminator selected from the group consisting of:
(1) all or a portion of a polynucleotide having the nucleotide sequence indicated in SEQ ID NO: 10, and
(2) a polynucleotide that hybridizes with all or a portion of the polynucleotide having the nucleotide sequence indicated in SEQ ID NO: 10 under stringent conditions and functions as a terminator of a coding region of flavonoid 3'5'-hydroxylase (F3'5'H).

[4] The F3'5'H gene construct described in [3] above selected from the group consisting of:
(1) a polynucleotide having the nucleotide sequence indicated in SEQ ID NO: 6, and
(2) a polynucleotide that hybridizes with the polynucleotide having the nucleotide sequence indicated in SEQ ID NO: 6 under stringent conditions and is able to express flavonoid 3',5'-hydroxylase (F3'5'H) in petunias or chrysanthemums.

[5] A vector comprising the petal-specific promoter described in [1] above or the F3'5'H gene construct described in any of [2] to [4] above.

[6] A microorganism containing the vector described in [5] above.

[7] A plant introduced with the petal-specific promoter described in [1] above or the F3'5'H gene construct described in any of [2] to [4] above, a tissue thereof, a progeny thereof or a vegetative growth form thereof.

A gene construct for inhibiting expression of a gene by RNAi having a polynucleotide that is all or a portion of a first intron at position 3093 to position 3617 of the nucleotide sequence indicated in SEQ ID NO: 6 in a loop.

[9] The gene construct described in [8] above, wherein the gene for which expression is inhibited is flavonoid 3'-hydroxylase.

[10] A plant introduced with the gene construct described in [9] above, an organ thereof, a tissue thereof, a progeny thereof or a vegetative growth form thereof.

[11] The plant described in [10] above, in which the flavonoid content thereof has changed before and after the introduction, an organ thereof, a tissue thereof, a progeny thereof or a vegetative growth form thereof.

[12] The plant described in [10] above, in which the delphinidin content thereof has changed before and after the introduction, an organ thereof, a tissue thereof, a progeny thereof or a vegetative growth form thereof.

[13] The plant described in [10] above, in which the pelargonidin content thereof has changed before and after the introduction, an organ thereof, a tissue thereof, a progeny thereof or a vegetative growth form thereof.

[14] The plant described in [10] above, in which the flower color thereof has changed before and after the introduction, or progeny thereof.

Effects of the Invention

The novel *cineraria*-derived polynucleotide able to function as a promoter of a coding region of flavonoid 3',5'-hydroxylase (F3'5'H), and the novel F3'5'H gene construct comprising the polynucleotide, according to the present invention can be preferably used as a tool for changing petal color.

In addition, the sequence of an intron of the novel *cineraria*-derived polynucleotide able to function as a promoter of a coding region of flavonoid 3',5'-hydroxylase (F3'5'H) according to the present invention (polynucleotide that is all or a portion of a first intron at position 3093 to position 3617 of the nucleotide sequence indicated in SEQ ID NO: 6) can be preferably used as a loop sequence in a gene construct for inhibiting expression of a gene by RNAi.

BRIEF DESCRIPTION OF THE DRAWINGS

FIG. 5 is a structural schematic diagram of a vector pCGP3620 for plant transformation.

BEST MODE FOR CARRYING OUT THE INVENTION

Figure 1:
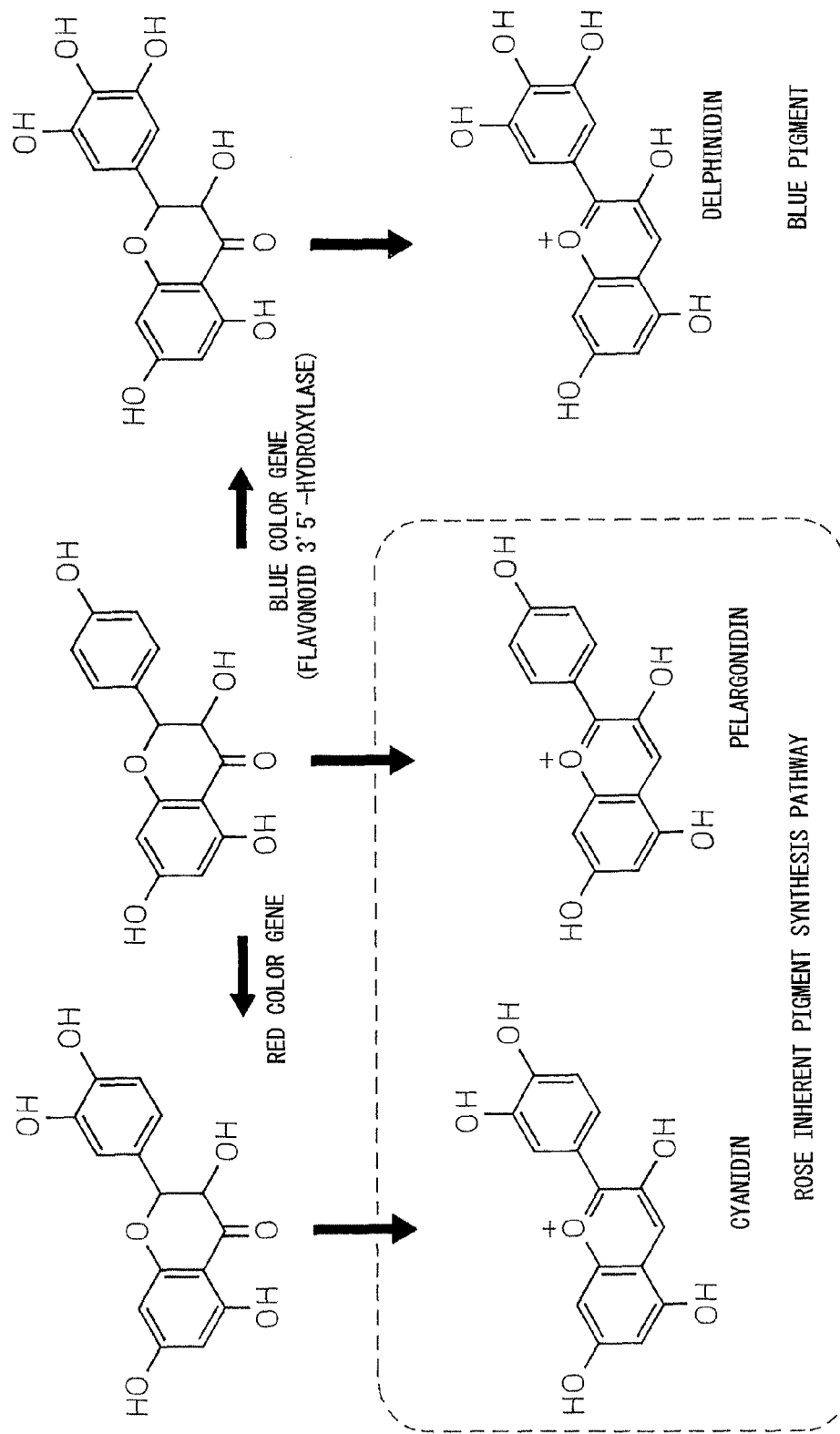
FIG. 1 is a schematic diagram of pathways of rose flower color pigment synthesis.

The following provides a more detailed explanation of the present invention.

In the present specification, a "polynucleotide that hybridizes under stringent conditions" refers to a polynucleotide obtained by using colony hybridization, plaque hybridization or southern blot hybridization and the like, and an example thereof is a DNA that can be immobilized by allowing a probe (such as polynucleotide having the nucleotide sequence indicated in SEQ ID NO: 6) to act on a support immobilized with a polynucleotide to be detected, carrying out hybridization for 2 hours at 42° C. in the presence of 0.7 to 1.0 M NaCl, followed by carrying out hybridization for 12 to 16 hours at 42° C. in the presence of 0.7 to 1.0 M NaCl, and washing the filter at 42° C. using a roughly 0.1 to 2-fold SSC solution (the composition of a 1-fold concentration SSC solution consisting of 150 mM sodium chloride and 15 mM sodium citrate). Hybridization can be carried out in compliance with, for example, the method described in Molecular Cloning: A Laboratory Manual, 2nd edition (Cold Spring Harbor Laboratory, Cold Spring Harbor, N.Y., 1989).

In addition, an example of hybridization conditions is low stringent conditions. Low stringent conditions refer to conditions of, for example, conditions of 0.1% SDS at 5×SSC and 42°, and preferably conditions of 0.1% SDS at 5×SSC and 50° C., during washing following hybridization. More preferably, high stringent conditions are used for the hybridization conditions. High stringent conditions refer to, for example, conditions of 0.1% SDS at 0.1×SSC and 65° C. Under these conditions, DNA having high homology can be expected to be efficiently obtained as the temperature is raised. However, a plurality of factors such as temperature or salt concentration are thought to influence the stringency of hybridization, and similar stringency can be realized by a person with ordinary skill in the art by suitably selecting these factors.

An example of a DNA that hybridizes under stringent conditions is a DNA having a certain sequence identity or higher with the nucleotide sequence of a DNA used as a probe, and the sequence identity is, for example, 70% or higher, preferably 80% or higher, more preferably 90% or higher, even more preferably 93% or higher, particularly preferably 95% or higher, and most preferably 98% or higher.

Examples

The following provides a detailed explanation of the present invention through non-limiting examples.

Example 1

Acquisition of *Cineraria* CYP75B Gene

RNA was extracted from the petals of blue *cineraria* Senetti (Suntory Flowers) buds in accordance with ordinary methods. A cDNA library was produced using poly-A+RNA prepared from this RNA using the ZAP-cDNA® Library Construction Kit (Stratagene, Product No. 200450) in accordance with the method recommended by the manufacturer. This cDNA library was then screened using butterfly pea F3'5'H cDNA (*Clitoria ternatea*) (see Plant Biotechnology, 23, 5-11 (2006)) labeled with the DIG System (Roche Applied Science) in accordance with the method recommended by the manufacturer. The resulting phages demonstrating 48 signals were purified. Plasmids were obtained from these phages by in vivo excision in accordance with the method recommended by the manufacturer (Stratagene).

The nucleotide sequences of the cDNA moieties contained in these plasmids were determined, numerous genes that demonstrated homology with cytochrome P450 were able to be obtained when a Blast search was performed of DNA databases, and the genes were able to be classified into 8 types. The complete nucleotide sequences of two clones (Ci5a13 (SEQ ID NO: 1) and Ci5a18 (SEQ ID NO: 2)) that were presumed to be classified as CYP75B were respectively determined.

Example 2

Functional Analysis of Acquired Genes Ci5a13 and Ci5a18

Each cDNA moiety of Ci5a13 and Ci5a18 was inserted between a constitutive promoter, MacI promoter (see Plant Molecular Biology, 15: 373-381, 1990), on a binary vector pBinPLUS (see Trangenic Research, 4: 288-290, 1995) and a mannopine synthase terminator, and were respectively designated as pSPB2875 and pSPB2786.

The resulting binary vectors were transformed in petunia strain Skr4×Sw63 using the *Agrobacterium* method. Japanese Patent No. 308726 should be referred to regarding the transformation method and petunia strain. Several stains of the transformed petunias exhibited a darker flower color than the host. When the strains were analyzed for anthocyanidin, levels of cyanidin and its derivative, peonidin, were markedly increased in strains introduced with Ci5a13, while in strains introduced with Ci5a18, levels of delphinidin and its derivatives, petunidin and malvidin, were markedly increased. Thus, Ci5a13 was determined to encode F3'H while Ci5a18 was determined to encode F3'5'H. The following Table 1 shows the analyzed values (number of μg per g of flower petal) of pelargonidin, cyanidin, peonidin, delphinidin, petunidin and malvidin in flower petals of the petunia transformants.

TABLE 1

| | Petunia | | | | | |
|---|---|---|---|---|---|---|
| | Pelargonidin (μg/g) | Cyanidin (μg/g) | Peonidin (μg/g) | Delphinidin (μg/g) | Petunidin (μg/g) | Malvidin (μg/g) |
| Pre-transformed host | 20 | 0 | 12 | 0 | 5.3 | 91 |
| Introduction of Ci5a13 | | | | | | |
| Exp. No. 9 | 1.5 | 2.5 | 520 | 0 | 2.5 | 87 |
| Exp. No. 23 | 2.3 | 5.6 | 550 | 0 | 5.6 | 130 |
| Introduction of Ci5a18 | | | | | | |
| Exp. No. 4 | 12 | 1.6 | 40 | 7.8 | 66 | 570 |
| Exp. No. 12 | 7.8 | 11 | 91 | 11 | 86 | 700 |

Example 3

Acquisition of *Cineraria* Chromosome Clones

Chromosomal DNA was extracted from the same *cineraria* leaves of Example 1, and a chromosome library was produced using the λBlueSTAR™ Xho I Half-Site Arms Kit (Novagen). The resulting 200,000 plaques were screened using a Ci5a18 cDNA fragment labeled with DIG. This cDNA fragment was amplified using primers (Ci5a18F1 (SEQ ID NO: 7): 5'-CATCTGTTTTCTGCCAAAGC-3' and Ci5a18R1 (SEQ ID NO: 8): 5'GGATTAGGAAACGAC-CAGG-3') as primers and using Ci5a18 as a template. Four plaques were ultimately obtained from the resulting 17 plaques, and these were converted to plasmids by in vivo excision. When their DNA nucleotide sequences were determined, they were found to contain the same sequence. Among these, clones obtained using gCi01-pBluestar were used in subsequent experiments. The nucleotide sequence of a gCi01-pBluestar clone is shown in SEQ ID NO: 5. This sequence was expected to contain a promoter region and translation region of *cineraria* F3'5'H. In the amino acid sequence of the translation region, four amino acids had changed from the Ci5a18 amino acid sequence shown in SEQ ID NO: 4. Namely, although residue nos, 151, 159, 161 and 329 of the Ci5a18 amino acid sequence (SEQ ID NO: 4) were methionine, glycine, glutamine acid and isoleucine, respectively, in the chromosomal clones, these consisted of threonine, arginine, glycine and valine (see SEQ ID NO: 6), Example 4

Functional Analysis of *Cineraria* Chromosome Clones in *Cineraria*

Figure 2:
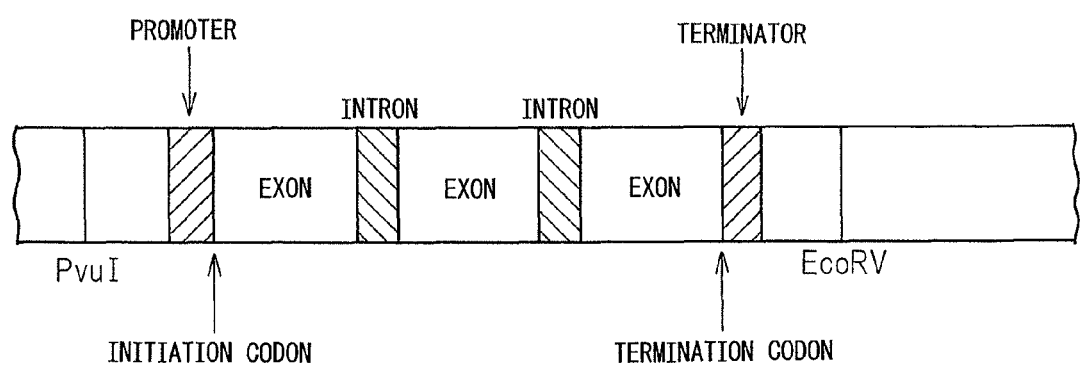
FIG. 2 is a structural schematic diagram of an F3'5'H gene construct according to the present invention.

A DNA fragment of about 5.7 kb excised from gCi01-pBluestar with PvuI and EcoRV (SEQ ID NO: 6) was blunt-ended using a DNA blunting kit (Takara). This DNA fragment was then cloned to an SmaI site of pBinPLUS and designated as pSPB3130. FIG. 2 indicates the structure of the DNA fragment of about 5.7 kb (SEQ ID NO: 6) excised from gCi01-pBluestar with PvuI and EcoRV.

This binary vector had nptII gene that can be used to select T-DNA regions with kanamycin.

When this binary vector was introduced into petunias using the method described in Example 2, flower color became darker than that of the host. Typical results for anthocyanidins are shown in the following Table 2.

TABLE 2

| | Petunia | | | | | |
|---|---|---|---|---|---|---|
| | Pelargonidin (μg/g) | Cyanidin (μg/g) | Peonidin (μg/g) | Delphinidin (μg/g) | Petunidin (μg/g) | Malvidin (μg/g) |
| Pre-transformed host | 16 | 0 | 10 | 0 | 3.6 | 70 |
| Exp. No. 12 | 11 | 1.2 | 28 | 1.2 | 35 | 670 |
| Exp. No. 24 | 4.3 | 2.3 | 40 | 7.0 | 170 | 1300 |

In addition, RNA was extracted from the leaves and flowers of recombinant petunias (by dividing the growth stages into five stages, see Nature, 366: 276-279 (1993)) using RNeasy-Plant (Qiagen), and transcription products derived from introduced genes were amplified by RT-PCR (consisting of reverse transcription using Superscript 2 First Strand System (Invitrogen) followed by amplification by PCR). The previously described Ci5a18F1 (SEQ ID NO: 7) and Ci5a18R1 (SEQ ID NO: 8) were used for the primers. Transcription products were not detected in the leaves. The most transcription products were detected in the flower petals at stage 3 (time at which the petals start to open). Flower petal stage 3 is the time at which structural genes involved in flavonoid synthesis relating to flower color are expressed at the highest levels (see Plant Physiol., 132: 1652-1663, 2003). The above results indicate that a DNA sequence derived from a chromosome gene of F3'5'H of *cineraria* of the aster family (containing a promoter, translation region and terminator) (SEQ ID NO: 6) functions in petunias of the aster family, or in other words, that the promoter according to the present invention indicated in SEQ ID NO: 9 is suitable for controlling a structural gene involved in flavonoid synthesis relating to flower color. In classifying plants of the aster family and potato family, the plants are not necessarily closely related, and they respectively belong to different orders consisting of the order Asterales and the order Solanales. This means that a DNA sequence derived from a chromosome gene of the aster family was demonstrated to have function in a plant of a different order. A genetically modified plant obtained in this manner can be increased by vegetative growth such as bud cutting. In addition, the introduced gene is inserted into chromosomal DNA of the host plant, is transmitted to progeny, and normally demonstrates a phenotype even in the progeny.

Example 5

Expression of *Cineraria* Chromosome Clones in Chrysanthemums

A DNA fragment (SEQ ID NO: 6) of about 5.7 kb excised from gCi01-pBluestar (SEQ ID NO: 5) with PvuI and EcoRV was inserted into an SmaI site of pCGP1988 (see PCT/AU03/01111) to obtain pCGP3141. This binary vector was introduced into the chrysanthemum variety, Improved Regan, according to the *Agrobacterium* method. Chrysanthemum transformation was carried out in accordance with, for example, the method described in International Publication WO94/28140, although not limited thereto. When flower petals of the chrysanthemum that bloomed were analyzed, delphinidin was detected at about 5% that is not contained in the host. Thus, a DNA sequence originating in a F3'5'H chromosome gene of *cineraria* (including a promoter, translation sequence and terminator) (SEQ ID NO: 6) was indicated to have actually functioned in chrysanthemum. A genetically modified plant obtained in this manner can be increased by vegetative growth such as bud cutting. In addition, the introduced gene is inserted into chromosomal DNA of the host plant, is transmitted to progeny, and normally demonstrates a phenotype even in the progeny.

Example 6

Construction of pCGP3618 pCGP3618 comprises an expression cassette containing rose chalcone synthase promoter, pansy F3'5'H #18 and nopaline synthase terminator, and an expression cassette containing an inverted repeat sequence of chrysanthemum F3'H gene containing rose chalcone synthase promoter and an intron of *cineraria* F3'5'H gene, and a nopaline synthase terminator. This vector was constructed with the intent of inhibiting expression of F3'H gene in chrysanthemum while simultaneously expressing F3'5'H gene.

The following provides a stepwise description of the construction process.
<Construction of pCGP3445 Containing First Intron of *Cineraria* F3'5'H Gene>

A DNA fragment of about 569 bp containing a first intron from position 3090 to position 3617 of the nucleotide sequence shown in SEQ ID NO: 6 of *cineraria* F3'5'H gene was amplified using plasmid gCi01 as a template and using the following synthetic DNA primers:
 CinF 5146-5170S
 (5'-GCATCCCGGGAGTTCGACAGGTTTTG-
  TACTTTTCAC-3')
 (SEQ ID NO: 11) (containing sequence from position
  3083 to position 3107 from SEQ ID NO: 6, and
  recognition sequence of restriction enzyme SmaI); and,
 CinR 5670-5690RV
 (5'GCATGTCGACGATATACACCTCCTCCTG-
  TAGTTACG-3')
 (SEQ ID NO: 12) (containing complementary sequence
  of the sequence from position 3606 to position 3624
  of SEQ ID NO: 6 and recognition sequence of restriction
  enzymes SalI and EcoRV).

This 569 bp DNA fragment was sub-cloned to plasmid pCR2.1 (Invitrogen), and the resulting plasmid was designated as pCGP3445.
<Construction of Plasmid pCGP3602 (Intron of *Cineraria* F3'S'H Gene Linked to Rose CHS Promoter and Nopaline Synthase Terminator)> pCGP3445 was digested with XhoI and SalI, and a DNA fragment of about 560 bp was recovered. This DNA fragment was inserted into pCGP2203 digested with XhoI (described in PCT/AU2008/001694, consisting of pansy F3'5'H #18 cDNA inserted between rose CHS promoter and nos terminator), and the resulting plasmid was further digested with SmaI to remove the roughly 260 bp DNA fragment derived from pansy F3'S'H #18 cDNA. The resulting plasmid was designated as pCGP3602.
<Construction of Plasmid pCGP3609 (Rose CHS Promoter+Forward Chrysanthemum F3'H cDNA+Intron of *Cineraria* F3'5'H Gene+Nopaline Synthase Terminator)>

Plasmid pCGP3133 (described in PCT/AU2008/001694, containing a portion of chrysanthemum F3'H gene amplified by PCR followed by addition of an XhoI sequence to both ends thereof) was digested with NcoI and BamHI, and the resulting roughly 1.1 kb DNA fragment was recovered and blunted followed by inserting into an SmaI site of pCGP3602. A plasmid in which cDNA was linked in the forward direction downstream from a promoter was designated as pCGP3609.
<Construction of Plasmid pCGP3613 (Rose CHS Promoter+Forward Chrysanthemum F3'H cDNA+Intron of *Cineraria* F3'5'H Gene+Reverse Chrysanthemum F3'H cDNA+Nopaline Synthase Terminator)>

A roughly 1.1 kb DNA fragment obtained by digesting plasmid pCGP3133 with XbaI was blunted followed by insertion into an EcoRV site of pCGP3609. The plasmid in which cDNA was inserted in the reverse direction was designated as pCGP3613. The DNA construct consisting of forward chrysanthemum F3'H cDNA+intron of *cineraria* F3'S'H gene+reverse chrysanthemum F3'H cDNA is hereinafter also referred to as ds chrysanthemum F3'H (*cineraria* intron 1).
<Construction of Transformation Plasmid pCGP3618 (Rose CHS Promoter+Pansy F3'5'H #18+Nopaline Synthase Terminator; Rose CHS Promoter+ds Chrysanthemum F3'H (*Cineraria* Intron 1)+Nopaline Synthase Terminator)>

Figure 3:
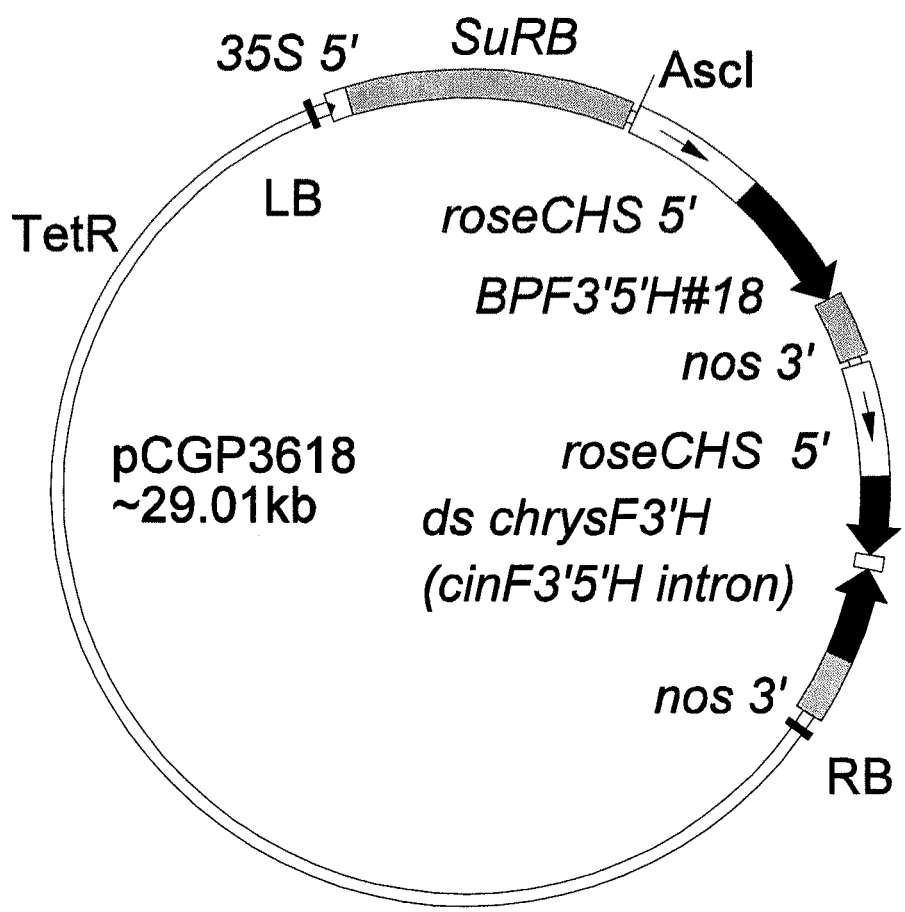
FIG. 3 is a structural schematic diagram of a vector pCGP3618 for plant transformation.

A DNA fragment containing rose CHS promoter+ds chrysanthemum F3'H (*cineraria* intron 1)+nopaline synthase terminator was recovered from pCGP3613 by digesting with restrictases BglII and NotI. This DNA fragment was then blunted and linked with a DNA fragment obtained by digesting pCGP2217 (described in PCT/AU2008/001694) with PmeI to obtain plant transformation vector pCGP3618 shown in FIG. 3.

Example 7

Construction of Transformation Vector pCGP3617 (Rose CHS Promoter+ds Chrysanthemum F3'H (*Cineraria* Intron 1)+Nopaline Synthase Terminator)

Figure 4:
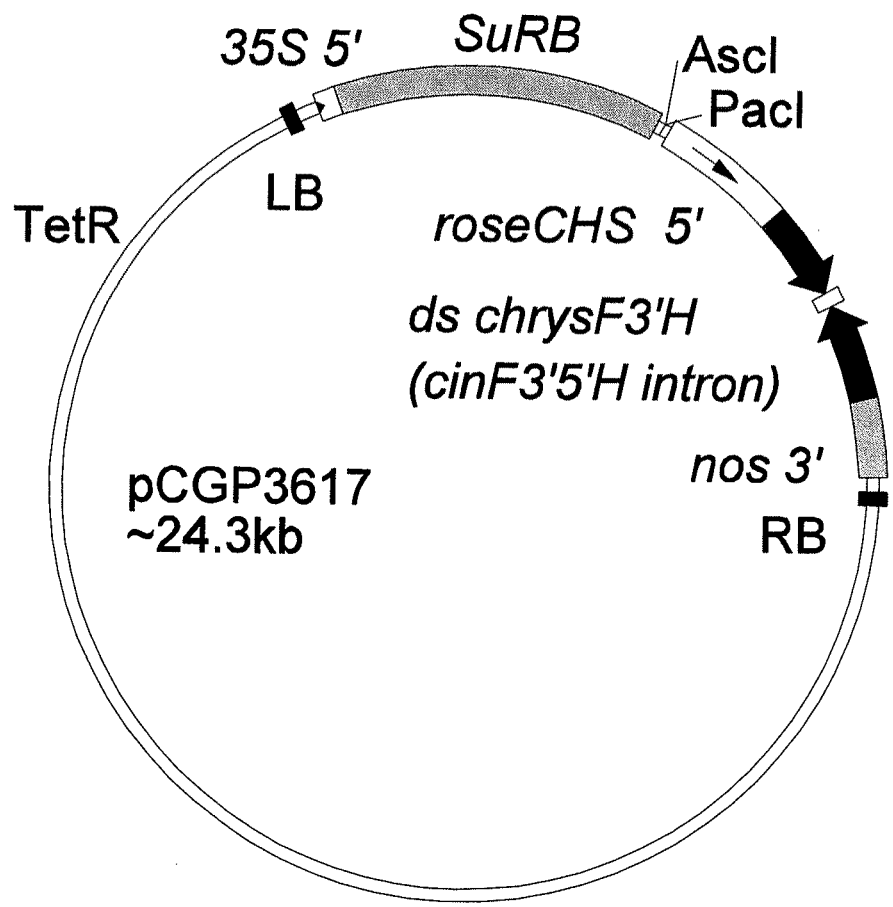
FIG. 4 is a structural schematic diagram of a vector pCGP3617 for plant transformation.

A DNA fragment containing rose CHS promoter+ds chrysanthemum F3'H (*cineraria* intron 1)+nopaline synthase terminator was recovered from pCGP3613 by digesting with restrictases BglII and NotI. This DNA fragment was then blunted and linked with a DNA fragment obtained by digesting pCGP1988 (described in PCT/AU03/01111) with PmeI to obtain a plant transformation vector pCGP3617 shown in FIG. 4.

Example 8

Construction of Transformation Vector pCGP3620 (Promoter Region of *Cineraria* F3'5'H+Pansy F3'5'H #18 cDNA+Nopaline Synthase Terminator)<

Construction of pCGP3604 (Promoter Region of *Cineraria* F3'5'H)>

A DNA sequence of the promoter region of *cineraria* F3'5'H was amplified by PCR using plasmid gCi1, containing *cineraria* F3'5'H chromosomal DNA, as a template and using the following synthetic DNA as primers:

CinF 3113-3128RV (5'-GAAATGTGTAAGGGTG-CAGCTGC-3') (SEQ ID NO: 13 (containing a PvuII recognition site);
and,
CinR 4694-4714R1 (5'-TTTATTTACTTGACAACG-TAAGAATTCGTTAGTAATTATAGG-3') (SEQ ID NO: 14) (containing an EcoRI recognition site).

The resulting roughly 1.5 kb DNA fragment was linked with a DNA fragment obtained by blunting pBluescript KS+ digested with EcoRI. The resulting plasmid was designated as pCGP3604.

<Construction of pCGP3615 (*Cineraria* F3'5'H Promoter Region+Pansy F3'5'H #18 cDNA+Nopaline Synthase Terminator)>

A DNA fragment (approx. 1.9 kb) containing pansy F3'5'H #18 cDNA+nopaline synthase terminator was recovered by digesting plasmid pCGP2203 with EcoRI and NotI. This DNA fragment was linked with pCGP3604 digested with EcoRI and NotI to obtain plasmid pCGP3615.

<Construction of Transformation Vector pCGP3620 (*Cineraria* F3'5'H Promoter Region+Pansy F3'5'H #18 cDNA+Nopaline Synthase Terminator)>

Plasmid pCGP3615 was digested with NotI and blunted. An roughly 3.6 kb DNA fragment was obtained by further digesting with EcoRV. This DNA fragment was then linked with pCGP1988 digested with PmeI to obtain plant transformation binary vector pCGP3620 shown in FIG. 5.

Example 9

Production of Pelargonidin in Chrysanthemum>

T-DNA moieties of pCGP3246 and pCGP3617 were inserted into chrysanthemum variety, Improved Regan, as described in Example 5. Flower color of flowers of the transformant changed from the pink color of Improved Regan to an apricot color. In addition, pelargonidin, which is not contained in flowers of the Improved Regan variety, was contained in flowers of the transformant. In contrast to the content of pelargonidin (ratio of pelargonidin to total amount of anthocyanidins) of the transformant derived from pCGP3426 being an average of about 17%, the content of pelargonidin in the transformant derived from pCGP3617 was an average of about 56%. In cases of having introduced either vector, pelargonidin was contained that is not contained in naturally-occurring chrysanthemums, and a new flower color was able to be obtained as a result thereof. This constitutes an industrially useful result. In addition, the use of a *cineraria* intron was determined to make it possible to efficiently inhibit F3'H gene while also making it possible to demonstrate a more prominent change in flower color.

Example 10

Production of Delphinidin in Chrysanthemum

T-DNA moieties of pCGP3429 (Rose CHS Promoter+ Pansy F3'5'H #18 cDNA+Nopaline Synthase Terminator; rose CHS promoter+ds chrysanthemum F3'H (not inserted with intron)+nopaline synthase terminator, described in PCT/AU2008/001694) and pCGP3618 (described in Example 6) were introduced into the chrysanthemum variety, Improved Regan, as described in Example 5. Flower color of the resulting transformant become bluer in comparison with the Improved Regan variety. In addition, delphinidin was produced that is not contained in Improved Regan. In contrast to the delphinidin content of the transformant derived from pCGP3429 being about 26% to 64%, the delphinidin content of the transformant derived from pCGP3618 reached a maximum of 80%. Chrysanthemum endogenous F3'H and externally introduced F3'5'H are thought to hydrolyze the same substrate (such as dihydrokaempferol) and be used in the synthesis of cyanidin and delphinidin, respectively. Enhancing expression of F3'5'H as well as inhibiting activity of F3'H are effective for enhancing delphinidin content. The high content of delphinidin in chrysanthemums introduced with pCGP3618 as compared with that in those introduced with pCGP3429 suggests that the *cineraria* intron sequence is effective in inhibiting expression of F3'H gene.

INDUSTRIAL APPLICABILITY

The novel *cineraria*-derived polynucleotide according to the present invention that is able to function as a promoter of a coding region of flavonoid 3',5'-hydroxylase (F3'5'H), and a novel F3'5'H gene construct containing this polynucleotide, can be preferably used as a tool for changing flower color.

In addition, an intron sequence (polynucleotide that is all or a portion of a first intron from position 3093 to position 3617 of the nucleotide sequence shown in SEQ ID NO: 6) of the novel *cineraria*-derived polynucleotide according to the present invention that is able to function as a promoter of a coding region of flavonoid 3',5'-hydroxylase (F3'5'H) can be preferably used as a loop sequence in a gene construct for inhibiting gene expression by RNAi.

BRIEF DESCRIPTION OF THE REFERENCE SYMBOLS

35S: Cauliflower mosaic virus 35S promoter
LB: Left border
SuRB: Tobacco acetolactate synthase
Rose CHS: Rose chalcone synthase 5'-untranslated sequence (=promoter)
BPF3'5'H #18: Black pansy F3'5'H #18 gene
nos: Nopaline synthase 3'-untranslated sequence
ds chrys F3'H: Double-stranded chrysanthemum F3'H cinF3'5'H intron: *Cineraria* F3'5'H gene intron
RB: Right border
TetR: Tetracycline resistance gene ds chrys F3'H: Double-stranded chrysanthemum F3'H
CinF3'5'H5': *Cineraria* F3'5'H gene 5'-untranslated region (=promoter)

The invention claimed is:

1. A vector comprising a petal-specific promoter, wherein the petal-specific promoter comprises the nucleotide sequence of SEQ ID NO: 9 and is operably linked to a gene that is not naturally linked to the petal-specific promoter.

2. A microorganism containing the vector according to claim 1.

3. A transgenic plant, wherein the transgenic plant comprises a transgene comprising an exogenous gene operably linked to a petal-specific promoter, and wherein the petal-specific promoter comprises the nucleotide sequence of SEQ ID NO: 9.

4. An organ, a tissue, a progeny, or a vegetative growth form of a transgenic-plant, wherein the organ, tissue, progeny or vegetative growth form comprises a transgene, wherein the transgene comprises an exogenous gene operably linked to a petal-specific promoter and wherein the petal-specific promoter comprises the nucleotide sequence of SEQ ID NO: 9.

* * * * *